(12) United States Patent
Sundermann et al.

(10) Patent No.: US 7,592,351 B2
(45) Date of Patent: Sep. 22, 2009

(54) SUBSTITUTED IMIDAZO[1,2-A]PYRIDINE COMPOUNDS AND PHARMACEUTICAL PREPARATIONS CONTAINING SUBSTITUTED IMIDAZO[1,2-A]PYRIDINE COMPOUNDS

(75) Inventors: Bernd Sundermann, Aachen (DE);
Corinna Sundermann, Aachen (DE);
Hagen-Heinrich Hennies, Simmerath (DE); Ruth Jostock, Stolberg (DE)

(73) Assignee: Gruenenthal GmbH, Aachen (DE)

( * ) Notice: Subject to any disclaimer, the term of this patent is extended or adjusted under 35 U.S.C. 154(b) by 117 days.

(21) Appl. No.: 11/589,146

(22) Filed: Oct. 30, 2006

(65) Prior Publication Data
US 2007/0099896 A1 May 3, 2007

Related U.S. Application Data

(63) Continuation of application No. PCT/EP2005/04528, filed on Apr. 28, 2005.

(30) Foreign Application Priority Data
Apr. 30, 2004 (DE) .................. 10 2004 021 716

(51) Int. Cl.
*A01N 43/42* (2006.01)
*A61K 31/44* (2006.01)
*C07D 491/02* (2006.01)
*C07D 498/02* (2006.01)

(52) U.S. Cl. ..................... 514/300; 546/121
(58) Field of Classification Search ............... 514/300; 546/121
See application file for complete search history.

(56) References Cited

U.S. PATENT DOCUMENTS 4,450,164 A * 5/1984 Bristol et al. ............... 514/303
6,020,342 A * 2/2000 Tanaka et al. ............... 514/292

OTHER PUBLICATIONS

Blackburn et al., Tetrahedron Letters (1998), 39(22), 3635-3638.*
Hudson et al., The European journal of neuroscience, (Jun. 2001), vol. 13, No. 11, pp. 2105-2114.*

* cited by examiner

*Primary Examiner*—D. Margaret Seaman
*Assistant Examiner*—Niloofar Rahmani
(74) *Attorney, Agent, or Firm*—Crowell & Moring LLP

(57) ABSTRACT

Substituted imidazo[1,2-a]pyridine compounds, a process for the production thereof, pharmaceutical preparations containing such compounds and methods of using such substituted imidazo[1,2-a]pyridine compounds to treat and/or inhibit various diseases or pathological conditions.

45 Claims, No Drawings

SUBSTITUTED IMIDAZO[1,2-A]PYRIDINE COMPOUNDS AND PHARMACEUTICAL PREPARATIONS CONTAINING SUBSTITUTED IMIDAZO[1,2-A]PYRIDINE COMPOUNDS

CROSS REFERENCE TO RELATED APPLICATIONS

This application is a continuation of international application no. PCT/EP2005/004528, filed Apr. 28, 2005 designating the United States of America and published in German on Nov. 10, 2005 as WO 2005/105798, the entire disclosure of which is incorporated herein by reference. Priority is claimed based on Federal Republic of Germany patent application no. DE 10 2004 021 716.5, filed Apr. 30, 2004.

BACKGROUND OF THE INVENTION

The present invention relates to substituted imidazo[1,2-a]pyridine compounds, to a process for the production thereof, to pharmaceutical preparations containing these compounds and to the use of substituted imidazo[1,2-a]pyridine compounds for the production of pharmaceutical preparations.

The treatment of pain, in particular of neuropathic pain, is of great significance in medicine. There is a worldwide need for effective pain treatments. The urgency of the requirement for effective therapeutic methods for providing tailored and targeted treatment of chronic and non-chronic pain, this being taken to mean pain treatment which is effective and satisfactory from the patient's standpoint, is also evident from the large number of scientific papers relating to applied analgesia and to basic nociception research which have appeared in recent times.

One approach to the treatment of pain, in particular of neuropathic pain, is the vanilloid receptor subtype 1 (VR1), which is often also known as the capsaicin receptor. This receptor is stimulated inter alia by vanilloids such as for example capsaicin, heat and protons and plays a central role in the genesis of pain. It is furthermore of significance to numerous other physiological and pathophysiological processes, such as for example migraine, peripheral neuropathies, diabetic neuropathies, stroke, neurodegenerative diseases, Lewy body disease, brain injuries, nerve injuries, motor neurone diseases, convulsions in epilepsy, emesis, bulimia, high blood pressure, depression, glaucoma, urinary incontinence, diseases caused by prions, infectious rhinitis or interstitial cystitis.

SUMMARY OF THE INVENTION

One object of the present invention was accordingly to provide novel compounds, which are in particular suitable as pharmaceutical active ingredients in pharmaceutical preparations, preferably in pharmaceutical preparations for vanilloid receptor subtype 1 (VR1) regulation.

The novel compounds should preferably be suitable for the treatment of pain, in particular of neuropathic pain and/or cluster headaches, for the prevention and/or treatment of migraine, peripheral neuropathies, diabetic neuropathies, AIDS dementia, stroke, neurodegenerative diseases, preferably selected from the group consisting of Parkinson's disease, Huntington's chorea, Alzheimer's disease and multiple sclerosis, Lewy body disease, brain injuries, nerve injuries, motor neurone diseases, convulsions in epilepsy, emesis, disorders of food intake, preferably selected from the group consisting of bulimia, anorexia, cachexia and obesity, high blood pressure, depression, glaucoma, urinary incontinence, bladder hyperactivity, diseases caused by prions, infectious rhinitis or interstitial cystitis.

It has surprisingly now been found that the substituted imidazo[1,2-a]pyridine compounds corresponding to formulae I and Ia stated below exhibit an elevated affinity for vanilloid receptor subtype 1 (VR1). The substituted imidazo[1,2-a]pyridine compounds corresponding to formulae I and Ia below surprisingly also exhibit an elevated affinity for cannabinoid receptors, in particular for cannabinoid 1 (CB1) receptors.

The substituted imidazo[1,2-a]pyridine compounds corresponding to formulae I and Ia are accordingly in particular suitable as pharmaceutical active ingredients in pharmaceutical preparations for the prevention and/or treatment of disorders or diseases which are at least in part mediated via VR1 receptors and/or CB1 receptors.

The present invention accordingly provides substituted imidazo[1,2-a]pyridine compounds corresponding to formula (I):

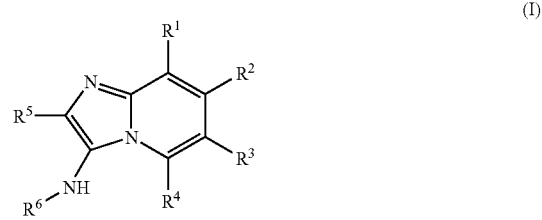

in which $R^1$, $R^2$, $R^3$ and $R^4$, identical or different, in each case denote hydrogen, halogen, a hydroxy group, a cyano group, a nitro group, an amino group, a carboxy group, a —C(=O)—$R^7$ group, a —(C=O)—$OR^8$ group, an $OR^9$ group, a linear or branched, saturated or unsaturated, optionally at least monosubstituted aliphatic residue, a saturated or unsaturated, optionally at least monosubstituted cycloaliphatic residue optionally attached via an alkylene group, or two adjacent residues $R^1$ and $R^2$, $R^2$ and $R^3$ or $R^3$ and $R^4$ in each case together form a 3- or 4-membered, saturated or unsaturated, aliphatic chain optionally comprising at least one heteroatom as a chain link, and the respective remaining residues $R^3$ and $R^4$, $R^1$ and $R^4$ or $R^1$ and $R^2$ denote hydrogen, $R^5$ denotes a linear or branched, saturated or unsaturated, optionally at least monosubstituted aliphatic residue, a saturated or unsaturated, optionally at least monosubstituted cycloaliphatic residue optionally comprising at least one heteroatom as a ring member, which cycloaliphatic residue is optionally attached via an alkylene group and may be fused with an optionally at least monosubstituted, mono- or polycyclic ring system, or an optionally at least monosubstituted aryl or heteroaryl residue optionally attached via an alkylene group, which aryl or heteroaryl residue may be fused with an optionally at least monosubstituted, mono- or polycyclic ring system, $R^6$ denotes a linear or branched, saturated or unsaturated, optionally at least monosubstituted aliphatic residue with more than 12 carbon atoms, $R^7$ denotes a linear or branched, saturated or unsaturated, optionally at least monosubstituted aliphatic residue, a saturated or unsaturated, optionally at least monosubstituted cycloaliphatic residue optionally comprising at least one heteroatom as a ring member, which cycloaliphatic residue is optionally attached via an alkylene group and may be fused with an optionally at least monosubstituted, mono- or polycyclic ring system, or an optionally at least monosubstituted aryl or heteroaryl residue optionally attached via an alkylene group, which aryl or heteroaryl residue may be fused with an optionally at least monosubstituted, mono- or polycyclic ring system, $R^8$ denotes a linear or branched, saturated or unsaturated, optionally at least monosubstituted aliphatic residue, a saturated or unsaturated, optionally at least monosubstituted cycloaliphatic residue optionally comprising at least one heteroatom as a ring member, which cycloaliphatic residue is optionally attached via an alkylene group and may be fused with an optionally at least monosubstituted, mono- or polycyclic ring system, or an optionally at least monosubstituted aryl or heteroaryl residue optionally attached via an alkylene group, which aryl or heteroaryl residue may be fused with an optionally at least monosubstituted, mono- or polycyclic ring system, $R^9$ denotes a linear or branched, saturated or unsaturated, optionally at least monosubstituted aliphatic residue, a saturated or unsaturated, optionally at least monosubstituted cycloaliphatic residue optionally comprising at least one heteroatom as a ring member, which cycloaliphatic residue is optionally attached via an alkylene group and may be fused with an optionally at least monosubstituted, mono- or polycyclic ring system, or an optionally at least monosubstituted aryl or heteroaryl residue optionally attached via an alkylene group, which aryl or heteroaryl residue may be fused with an optionally at least monosubstituted, mono- or polycyclic ring system, optionally in the form of the pure stereoisomers thereof, in particular enantiomers or diastereomers, the racemates thereof or in the form of mixtures of the stereoisomers, in particular the enantiomers and/or diastereomers, in any desired mixing ratio, or in each case in the form of corresponding salts or in each case in the form of corresponding solvates.

For the purposes of the present invention, a mono- or polycyclic ring system is taken to mean mono- or polycyclic hydrocarbon residues, which may be saturated, unsaturated or aromatic. If a polycyclic ring system is present, it may also comprise in different rings two or more corresponding substructures exhibiting a different degree of saturation, i.e. the particular rings may mutually independently be saturated, unsaturated or aromatic. A polycyclic ring system is preferably a bicyclic ring system. Such mono- or polycyclic ring systems may in each case be fused (i.e. anellated) with further cyclic residues such as for example cycloaliphatic residues, aryl residues or heteroaryl residues.

The mono- or polycyclic ring system may optionally also comprise one or more, for example 1, 2, 3, 4 or 5, heteroatoms as ring members, wherein the different rings of the polycyclic ring system may comprise identical or different heteroatoms, which may preferably in each case mutually independently be selected from the group consisting of oxygen, nitrogen and sulfur. If a polycyclic ring system is present, the individual rings thereof are preferably fused with one another. The rings of the mono- or polycyclic ring system are preferably in each case 5- or 6-membered.

Examples of aryl residues which are fused with a mono- or polycyclic ring system include [1,3]-benzodioxolyl, [1,4]-benzodioxanyl, [1,2,3,4]-tetrahydronaphthyl, [1,2,3,4]-tetrahydroquinolinyl, [1,2,3,4]-tetrahydroquinazolinyl and [3,4]-dihydro-2H-1,4-benzoxazinyl. Examples of cycloaliphatic residues which are fused with a mono- or polycyclic ring system include [1,2,3,4]-tetrahydronaphthyl, [1,2,3,4]-tetrahydroquinolinyl and [1,2,3,4]-tetrahydroquinazolinyl.

If a mono- or polycyclic ring system is mono- or polysubstituted, for example with 1, 2, 3, 4 or 5 substituents, the substituents thereof may, in each case mutually independently, preferably be selected from the group consisting of $C_{1-4}$ alkyl, $C_{1-4}$ alkoxy, hydroxy, halogen, —$CHF_2$, —$CH_2F$, —$CF_3$, phenyl, phenoxy, cyano, nitro, amino and di-($C_{1-3}$)-alkylamino, particularly preferably from the group consisting of methyl, ethyl, n-propyl, iso-propyl, n-butyl, sec-butyl, tert.-butyl, methoxy, ethoxy, n-propoxy, n-butoxy, tert.-butoxy, hydroxy, F, Cl, Br, —$CHF_2$, —$CH_2F$, —$CF_3$, phenyl, phenoxy, cyano, nitro, amino, dimethylamino and diethylamino.

Persons skilled in the art will understand that the number of atoms stated for a substituent in each case relates only to this substituent as such. In other words, an optionally at least monosubstituted aliphatic residue with more than 12 carbon atoms comprises more than 12 carbon atoms in the aliphatic moiety and may furthermore additionally bear one or more substituents which comprise further carbon atoms.

Suitable linear or branched, aliphatic residues with more than 12 carbon atoms include, for example, n-tridecanyl, n-tetradecanyl, n-pentadecanyl, n-hexadecanyl, n-heptadecanyl, n-octadecanyl, n-nonadecanyl, n-eicosanyl, (3,13)-dimethylhexadecanyl, (5,9)-dimethylhexadecanyl, 2-methylheptadecanyl, 5-methylheptadecanyl, 7-methylheptadecanyl, (3,12)-dimethylheptadecanyl, (5,11)-dimethylheptadecanyl, (7,11)-dimethylheptadecanyl, 2-methyloctadecanyl, n-heneicosanyl, n-docosanyl, n-tricosanyl, n-tetracosanyl, n-pentacosanyl, n-hexacosanyl, n-heptacosanyl, n-octacosanyl, n-noncosanyl and n-triacontanyl.

If one or more of the residues $R^1$-$R^9$ denote a linear or branched, saturated or unsaturated aliphatic residue, which is mono- or polysubstituted, for example with 1, 2, 3, 4 or 5 substituents, the substituents thereof may in each case mutually independently preferably be selected from the group consisting of $C_{1-4}$ alkoxy, hydroxy, halogen, —$CHF_2$, —$CH_2F$, —$CF_3$, phenyl, phenoxy, cyano, nitro, amino and di-($C_{1-3}$)-alkylamino, particularly preferably from the group consisting of methoxy, ethoxy, n-propoxy, n-butoxy, tert.-butoxy, hydroxy, F, Cl, Br, —$CHF_2$, —$CH_2F$, —$CF_3$, phenyl, phenoxy, cyano, nitro, amino, dimethylamino and diethylamino.

Suitable saturated or unsaturated aliphatic residues, i.e. alkyl, alkenyl and alkynyl residues, which may be mono- or polysubstituted, for example with 1, 2, 3, 4 or 5 substituents, include, for example, methyl, ethyl, n-propyl, iso-propyl, n-butyl, iso-butyl, sec-butyl, tert.-butyl, n-pentyl, iso-pentyl, neopentyl, n-hexyl, 2-hexyl, n-heptyl, n-octyl, 1,1,3,3-tetramethylbutyl, n-nonyl, n-decyl, n-uncedyl, n-dodecyl, vinyl, propenyl, propynyl, butenyl, butynyl, pentenyl, pentynyl, hexenyl, hexynyl, octenyl or octynyl.

If one or more of the residues $R^1$-$R^5$ and $R^7$-$R^9$ denote a saturated or unsaturated cycloaliphatic residue optionally attached via an alkylene group and optionally comprising at least one heteroatom as a ring member, which cycloaliphatic residue is mono- or polysubstituted, for example with 1, 2, 3, 4, or 5 substituents, the substituents thereof may, in each case mutually independently, preferably be selected from the group consisting of $C_{1-4}$ alkyl, $C_{1-4}$ alkoxy, hydroxy, halogen, —$CHF_2$, —$CH_2F$, —$CF_3$, phenyl, phenoxy, cyano, nitro, amino and di-($C_{1-3}$)-alkylamino, particularly preferably from the group consisting of methyl, ethyl, n-propyl, iso-propyl, n-butyl, sec-butyl, tert.-butyl, methoxy, ethoxy, n-propoxy, n-butoxy, tert.-butoxy, hydroxy, F, Cl, Br, —CHF$_2$, —CH$_2$F, —CF$_3$, phenyl, phenoxy, cyano, nitro, amino, dimethylamino and diethylamino.

Suitable cycloaliphatic residues, which may be mono- or polysubstituted, for example with 1, 2, 3, 4 or 5 substituents, include, for example, cyclopropyl, cyclobutyl, cyclopentyl, cyclohexyl, cycloheptyl, cyclooctyl, cyclopentenyl, cyclohexenyl, cycloheptenyl, cyclooctenyl, imidazolidinyl, tetrahydrofuranyl (tetrahydrofuryl), piperidinyl, piperazinyl or morpholinyl.

If one or more of the residues $R^5$ and $R^7$-$R^9$ denote an aryl or heteroaryl residue optionally attached via an alkylene group, which aryl or heteroaryl residue is mono- or polysubstituted, for example with 1, 2, 3, 4, or 5 substituents, the substituents thereof may, in each case mutually independently, preferably be selected from the group consisting of $C_{1-4}$ alkoxy, $C_{1-4}$ alkyl, hydroxy, halogen, —CHF$_2$, —CH$_2$F, —CF$_3$, phenyl, phenoxy, cyano, nitro, amino and di-($C_{1-3}$)-alkylamino, particularly preferably from the group consisting of methyl, ethyl, n-propyl, iso-propyl, n-butyl, sec-butyl, tert.-butyl, methoxy, ethoxy, n-propoxy, n-butoxy, tert.-butoxy, hydroxy, F, Cl, Br, —CHF$_2$, —CH$_2$F, —CF$_3$, phenyl, phenoxy, cyano, nitro, amino, dimethylamino and diethylamino.

Examples of suitable aryl residues include phenyl, 1-naphthyl and 2-naphthyl. Suitable heteroaryl residues include, for example, pyrrolyl, indolyl, furyl (furanyl), benzo[b]furanyl, thienyl (thiophenyl), benzo[b]thienyl, pyrazolyl, imidazolyl, thiazolyl, thiadiazolyl, triazolyl, oxazolyl, isoxazolyl, pyridinyl, pyridazinyl, pyrimidinyl, pyrazinyl, pyranyl, indazolyl, purinyl, indolizinyl, quinolinyl, isoquinolinyl and quinazolinyl.

Suitable 5- or 6-membered heteroaryl residues include, in particular, pyrrolyl, furyl (furanyl), thienyl (thiophenyl), pyrazolyl, imidazolyl, thiazolyl, thiadiazolyl, triazolyl, oxazolyl, isoxazolyl, pyridinyl, pyridazinyl, pyrimidinyl, pyrazinyl and pyranyl.

If one or more of the residues $R^5$ and $R^7$-$R^9$ denote a cycloaliphatic residue or comprise a cycloaliphatic residue which contains one or more, for example 1, 2 or 3 heteroatoms as ring member(s), said heteroatoms may, mutually independently, preferably be selected from the group consisting of sulfur, oxygen and nitrogen.

If one or more of the residues $R^5$ and $R^7$-$R^9$ denote a heteroaryl residue or comprise a heteroaryl residue, the heteroatoms may, mutually independently, preferably be selected from the group consisting of sulfur, oxygen and nitrogen. The heteroaryl residue may preferably optionally comprise 1, 2, 3, 4 or 5 heteroatom(s) as ring member(s).

If two adjacent residues $R^1$ and $R^2$, $R^2$ and $R^3$ or $R^3$ and $R^4$, respectively, together form a 3- or 4-membered, saturated or unsaturated aliphatic chain which comprises one or more, for example 1 or 2, heteroatoms as chain link(s), these heteroatoms may, mutually independently, preferably be selected from the group consisting of sulfur, oxygen and nitrogen. Suitable chains include, for example, —CH=CH$_2$—CH$_2$, —CH$_2$—CH$_2$—CH$_2$—, —CH$_2$—CH$_2$—CH$_2$—CH$_2$—, —O—CH$_2$—O—, —NH—CH$_2$—CH$_2$—O—, —O—CH$_2$—CH$_2$—O—, —NH—CH$_2$—CH$_2$—S— and —S—CH$_2$—CH$_2$—S—. Persons skilled in the art will understand that if two adjacent residues $R^1$ and $R^2$, $R^2$ and $R^3$ or $R^3$ and $R^4$, respectively, together form a 3- or 4-membered, saturated or unsaturated, aliphatic chain optionally comprising at least one heteroatom as a chain link, this gives rise to a tricyclic ring system.

If one or more of the residues $R^1$ to $R^5$ and $R^7$ to $R^9$ comprise a linear or branched $C_{1-5}$ alkylene group, this may preferably be selected from the group consisting of —(CH$_2$)—, —(CH$_2$)$_2$—, —C(H)(CH$_3$)—, —C(CH$_3$)$_2$—, —(CH$_2$)$_3$—, —(CH$_2$)$_4$—, —(CH$_2$)$_5$—, —C(H)(C(H)(CH$_3$)$_2$)— and —C(C$_2$H$_5$)(H)—.

Preferred substituted imidazo[1,2-a]pyridine compounds corresponding to formula (I) are those in which $R^1$, $R^2$, $R^3$ and $R^4$ may be identical or different and respectively denote hydrogen, F, Cl, Br, a hydroxy group, a cyano group, a nitro group, an amino group, a carboxy group, a —C(=O)—$R^7$ group, a —(C=O)—OR$^8$ group, an OR$^9$ group, a linear or branched, saturated or unsaturated, optionally at least monosubstituted aliphatic $C_{1-12}$ residue, a saturated or unsaturated, optionally at least monosubstituted cycloaliphatic $C_{3-8}$ residue optionally attached via a $C_{1-8}$ alkylene group, or in which two adjacent residues $R^1$ and $R^2$, $R^2$ and $R^3$ or $R^3$ and $R^4$, respectively, together form a 3- or 4-membered, saturated or unsaturated, aliphatic chain optionally comprising at least one heteroatom as a chain link, and the respective remaining residues $R^3$ and $R^4$, $R^1$ and $R^4$ or $R^1$ and $R^2$ denote hydrogen, preferably hydrogen, F, Cl, Br, a hydroxy group, a carboxy group, a —C(=O)—$R^7$ group, a —(C=O)—OR$^8$ group, an OR$^9$ group or a linear or branched $C_{1-12}$ alkyl residue, particularly preferably hydrogen, F, Cl or a linear or branched $C_{1-4}$ alkyl residue, very particularly preferably H, Cl or a methyl group, and the respective remaining residues $R^5$ to $R^9$ have the above-stated meaning, in each case optionally in the form of the pure stereoisomers thereof, in particular enantiomers or diastereomers, the racemates thereof or in the form of mixtures of the stereoisomers, in particular the enantiomers or diastereomers, in any desired mixing ratio, or in each case in the form of corresponding salts or in each case in the form of corresponding solvates.

Further preferred substituted imidazo[1,2-a]pyridine compounds corresponding to formula (I) are those in which $R^5$ denotes a linear or branched, saturated or unsaturated, optionally at least monosubstituted aliphatic $C_{1-2}$ residue, a saturated or unsaturated, optionally at least monosubstituted cycloaliphatic $C_{3-8}$ residue optionally comprising at least one heteroatom as a ring member, which cycloaliphatic residue is optionally attached via a $C_{1-8}$ alkylene group and may be fused with an optionally at least monosubstituted, mono- or polycyclic ring system, or an optionally at least monosubstituted, 5- or 6-membered aryl or heteroaryl residue optionally attached via a $C_{1-8}$ alkylene group, which aryl or heteroaryl residue may be fused with an optionally at least monosubstituted, mono- or polycyclic ring system, preferably a linear or branched $C_{1-8}$ alkyl residue, a saturated or unsaturated, optionally at least monosubstituted cycloaliphatic $C_{3-8}$ residue optionally comprising at least one heteroatom as a ring member, which cycloaliphatic residue is optionally attached via a $C_{1-3}$ alkylene group, or an optionally at least monosubstituted, 5- or 6-membered aryl or heteroaryl residue optionally attached via a $C_{1-3}$ alkylene group, particularly preferably a residue selected from the group consisting of optionally at least monosubstituted phenyl, optionally at least monosubstituted furyl, optionally at least monosubstituted thienyl and optionally at least monosubstituted pyridyl, very particularly preferably a 2-furyl, 3-furyl, 2-thienyl, 3-thienyl, 2-pyridyl, 3-pyridyl, 4-pyridyl or phenyl residue, and the respective remaining residues $R^1$ to $R^4$ and $R^6$ to $R^9$ have the above-stated meaning, in each case optionally in the form of the pure stereoisomers thereof, in particular enantiomers or diastereomers, the racemates thereof or in the form of mixtures of the stereoisomers, in particular the enantiomers or diastereomers, in any desired mixing ratio, or in each case in the form of corresponding salts or in each case in the form of corresponding solvates.

Furthermore preferred substituted imidazo[1,2-a]pyridine compounds corresponding to formula (I) are those in which $R^6$ denotes a linear or branched, saturated or unsaturated, optionally at least monosubstituted aliphatic residue with 13-30 carbon atoms, preferably a linear or branched, saturated or unsaturated, optionally at least monosubstituted aliphatic residue with 13-25 carbon atoms, particularly preferably a linear or branched, saturated or unsaturated, optionally at least monosubstituted aliphatic residue with 13 to 20 carbon atoms, very particularly preferably a linear or branched, unsubstituted alkyl residue with 13 to 18 carbon atoms (particularly suitable linear, unsubstituted alkyl residues may accordingly be selected from the group consisting of —$(CH_2)_{12}$—$CH_3$, —$(CH_2)_{13}$—$CH_3$, —$(CH_2)_{14}$—$CH_3$, —$(CH_2)_{15}$—$CH_3$, —$(CH_2)_{16}$—$CH_3$, —$(CH_2)_{17}$—$CH_3$), and in each case the residues $R^1$ to $R^5$ and $R^7$ to $R^9$ have the above-stated meaning, in each case optionally in the form of the pure stereoisomers thereof, in particular enantiomers or diastereomers, the racemates thereof or in the form of mixtures of the stereoisomers, in particular the enantiomers or diastereomers, in any desired mixing ratio, or in each case in the form of corresponding salts or in each case in the form of corresponding solvates.

Further preferred substituted imidazo[1,2-a]pyridine compounds corresponding to formula (I) are those in which the residue $R^7$ denotes a linear or branched, saturated or unsaturated, optionally at least monosubstituted aliphatic $C_{1-8}$ residue, a saturated or unsaturated, optionally at least monosubstituted cycloaliphatic $C_{3-8}$ residue optionally comprising at least one heteroatom as a ring member, which cycloaliphatic residue is optionally attached via a $C_{1-8}$ alkylene group and may be fused with an optionally at least monosubstituted, mono- or polycyclic ring system, or an optionally at least monosubstituted, 5- or 6-membered aryl or heteroaryl residue optionally attached via a $C_{1-8}$ alkylene group, which aryl or heteroaryl residue may be fused with an optionally at least monosubstituted, mono- or polycyclic ring system, preferably a linear or branched $C_{1-4}$ alkyl residue, a saturated or unsaturated, optionally at least monosubstituted cycloaliphatic $C_{3-8}$ residue optionally comprising at least one heteroatom as a ring member, which cycloaliphatic residue is optionally attached via a $C_{1-3}$ alkylene group, or denotes an optionally at least monosubstituted, 5- or 6-membered aryl or heteroaryl residue optionally attached via a $C_{1-3}$ alkylene group, which aryl or heteroaryl residue may be fused with an optionally at least monosubstituted, mono- or polycyclic ring system, and the respective remaining residues $R^1$ to $R^6$, $R^8$ and $R^9$ have the above-stated meaning in each case optionally in the form of the pure stereoisomers thereof, in particular enantiomers or diastereomers, the racemates thereof or in the form of mixtures of the stereoisomers, in particular the enantiomers or diastereomers, in any desired mixing ratio, or in each case in the form of corresponding salts or in each case in the form of corresponding solvates.

Likewise preferred substituted imidazo[1,2-a]pyridine compounds corresponding to formula (I) are those in which the residue $R^8$ denotes a linear or branched, saturated or unsaturated, optionally at least monosubstituted aliphatic $C_{1-8}$ residue, a saturated or unsaturated, optionally at least monosubstituted cycloaliphatic $C_{3-8}$ residue optionally comprising at least one heteroatom as a ring member, which cycloaliphatic residue is optionally attached via a $C_{1-8}$ alkylene group and may be fused with an optionally at least monosubstituted, mono- or polycyclic ring system, or an optionally at least monosubstituted, 5- or 6-membered aryl or heteroaryl residue optionally attached via a $C_{1-8}$ alkylene group, which aryl or heteroaryl residue may be fused with an optionally at least monosubstituted, mono- or polycyclic ring system, preferably a linear or branched $C_{1-4}$ alkyl residue, a saturated or unsaturated, optionally at least monosubstituted cycloaliphatic $C_{3-8}$ residue optionally comprising at least one heteroatom as a ring member, which cycloaliphatic residue is optionally attached via a $C_{1-3}$ alkylene group, or an optionally at least monosubstituted, 5- or 6-membered aryl or heteroaryl residue optionally attached via a $C_{1-3}$ alkylene group, which aryl or heteroaryl residue may be fused with an optionally at least monosubstituted, mono- or polycyclic ring system, and the respective remaining residues $R^1$ to $R^7$ and $R^9$ have the above-stated meaning, in each case optionally in the form of the pure stereoisomers thereof, in particular enantiomers or diastereomers, the racemates thereof or in the form of mixtures of the stereoisomers, in particular the enantiomers or diastereomers, in any desired mixing ratio, or in each case in the form of corresponding salts or in each case in the form of corresponding solvates.

Further preferred substituted imidazo[1,2-a]pyridine compounds corresponding to formula (I) are those in which the residue $R^9$ denotes a linear or branched, saturated or unsaturated, optionally at least monosubstituted aliphatic $C_{1-8}$ residue, a saturated or unsaturated, optionally at least monosubstituted cycloaliphatic $C_{3-8}$ residue optionally comprising at least one heteroatom as a ring member, which cycloaliphatic residue is optionally attached via a $C_{1-8}$ alkylene group and may be fused with an optionally at least monosubstituted, mono- or polycyclic ring system, or an optionally at least monosubstituted, 5- or 6-membered aryl or heteroaryl residue optionally attached via a $C_{1-8}$ alkylene group, which aryl or heteroaryl residue may be fused with an optionally at least monosubstituted, mono- or polycyclic ring system, preferably a linear or branched $C_{1-4}$ alkyl residue, a saturated or unsaturated, optionally at least monosubstituted cycloaliphatic $C_{3-8}$ residue optionally comprising at least one heteroatom as a ring member, which cycloaliphatic residue is optionally attached via a $C_{1-3}$ alkylene group, or an optionally at least monosubstituted, 5- or 6-membered aryl or heteroaryl residue optionally attached via a $C_{1-3}$ alkylene group, which aryl or heteroaryl residue may be fused with an optionally at least monosubstituted, mono- or polycyclic ring system, and the respective remaining residues $R^1$ to $R^8$ have the above-stated meaning, in each case optionally in the form of the pure stereoisomers thereof, in particular enantiomers or diastereomers, the racemates thereof or in the form of mixtures of the stereoisomers, in particular the enantiomers or diastereomers, in any desired mixing ratio, or in each case in the form of corresponding salts or in each case in the form of corresponding solvates.

Particularly preferred substituted imidazo[1,2-a]pyridine compounds corresponding to formula I are those selected from the group consisting of:
hexadecyl-(6-methyl-2-pyridin-2-yl-imidazo[1,2-a]-pyridin-3-yl)-amine,
(6,8-dichloro-2-thiophen-3-yl-imidazo[1,2-a]pyridin-3-yl)-hexadecyl-amine, and the respective corresponding salts and solvates thereof.

The present invention also provides a process for the production of substituted imidazo[1,2-a]pyridine compounds the above-stated general formula I and optionally corresponding stereoisomers, according to which process at least one aminopyridine corresponding to formula II

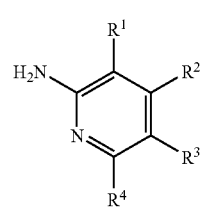

II in which the residues $R^1$ to $R^4$ have the above-stated meaning, is reacted with at least one aldehyde compound corresponding to formula III

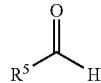

III in which $R^5$ has the above-stated meaning, and with at least one isonitrile corresponding to formula IV,

IV in which $R^6$ has the above-stated meaning, to yield a compound of the above-stated general formula I, and said latter compound is optionally purified and/or optionally isolated using methods known to persons skilled in the art.

The process according to the invention is preferably performed in a suitable reaction medium, preferably in an organic solvent, particularly preferably in methylene chloride and/or methanol or a solvent mixture based on methylene chloride and/or methanol.

The foregoing process for the production of substituted imidazo[1,2-a]pyridine compounds of formula I or of corresponding stereoisomers is performed in a three-component single vessel reaction, which may also be performed as a semi-automated or fully automated parallel synthesis. The process according to the invention is preferably performed in the presence of acid, preferably 20 wt.% strength perchloric acid. Temperature and pressure may vary over a wide range during performance of the process according to the invention. The process according to the invention is preferably performed at a temperature of 0° C. up to the boiling point of the reaction medium, preferably at 10 to 40° C. The process according to the invention is preferably performed under atmospheric pressure.

The particular starting compounds of formulas II, III and IV are commercially available or may be obtained by conventional processes known to persons skilled in the art.

If the substituted imidazo[1,2-a]pyridine compounds according to the invention are obtained after the production thereof in the form of the stereoisomers thereof, preferably in the form of the racemates thereof or other mixtures of their various enantiomers and/or diastereomers, these may be separated and optionally isolated by conventional processes known to persons skilled in the art. Examples which may be mentioned include chromatographic separation methods, in particular liquid chromatography methods at standard pressure or at elevated pressure, preferably MPLC and HPLC methods, and fractional crystallisation methods. In particular, individual enantiomers, for example diastereomeric salts formed by HPLC on a chiral phase or by crystallisation with chiral acids, for instance (+)-tartaric acid, (+31 )-tartaric acid or (+)-10-camphorsulfonic acid, may thus be separated from one another.

The substituted imidazo[1,2-a]pyridine compounds according to the invention corresponding to formula I and corresponding stereoisomers may be obtained using conventional processes known to persons skilled in the art in the form of the salts thereof, preferably the physiologically acceptable salts thereof, wherein the pharmaceutical preparations according to the invention stated below may comprise one or more salts of one or more substituted imidazo[1,2-a]pyridine compounds.

If the substituted imidazo[1,2-a]pyridine compounds according to the invention corresponding to formula I assume the form of basic salts, these are preferably salts of alkali metals, alkaline earth metals or ammonium salts, particularly preferably sodium, potassium, calcium, magnesium or ammonium salts, wherein ammonium salts are taken to mean not only $[NH_4]^+$ salts but also $[NH_xR_{4-x}]^+$ salts with $R=C_{1-4}$ alkyl and x=0+31 3, very particularly preferably sodium salts.

If the substituted imidazo[1,2-a]pyridine compounds according to the invention assume the form of acidic salts, these may be obtained, for example, by reaction with an inorganic or organic acid, preferably with hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid, saccharic acid, cyclohexanesulfamic acid, aspartame, monomethylsebacic acid, 5-oxo-proline, hexane-1-sulfonic acid, nicotinic acid, 2-, 3- or 4-aminobenzoic acid, 2,4,6-trimethylbenzoic acid, α-lipoic acid, acetylglycine, acetylsalicylic acid, hippuric acid and/or aspartic acid. The hydrochloride salts of the substituted imidazo[1,2-a]pyridine compounds according to the invention are particularly preferred.

The substituted imidazo[1,2-a]pyridine compounds corresponding to formula I and the corresponding stereoisomers thereof may, like the corresponding salts of these compounds, also be obtained in the form of the solvates thereof, preferably the hydrates thereof, using conventional processes known to persons skilled in the art.

It has now surprisingly been found that the substituted imidazo[1,2-a]pyridine compounds according to the invention corresponding to formula I and the stereoisomers, corresponding salts and corresponding solvates thereof exhibit an affinity for vanilloid receptor subtype 1 (VR1) and for cannabinoid receptor 1 (CB1). The substituted imidazo[1,2-a] pyridine compounds according to the invention of the above-stated general formula I and the stereoisomers, corresponding salts and corresponding solvates thereof are toxicologically safe and are suitable as pharmaceutical active ingredients in pharmaceutical preparations.

The present invention accordingly also provides pharmaceutical preparations containing at least one substituted imidazo[1,2-a]pyridine compound according to the invention corresponding to formula I, optionally in the form of one of the pure stereoisomers thereof, in particular enantiomers or diastereomers, the racemate thereof or in the form of mixtures of the stereoisomers, in particular the enantiomers or diastereomers, in any desired mixing ratio, or in each case in the form of a corresponding salt or in the form of a corresponding solvate, and optionally one or more physiologically acceptable auxiliary substances.

The pharmaceutical preparations according to the invention may furthermore contain as a further pharmacological active ingredient at least one substituted imidazo[1,2-a]pyridine compound corresponding to formula Ia stated below, optionally in the form of one of the pure stereoisomers thereof, in particular enantiomers or diastereomers, the racemate thereof or in the form of mixtures of the stereoisomers, in particular the enantiomers or diastereomers, in any desired mixing ratio, or in each case in the form of a corresponding salt or in the form of a corresponding solvate.

The pharmaceutical preparations according to the invention are suitable for vanilloid receptor 1 (VR1) regulation, for cannabinoid receptor 1 (CB1) regulation, for the treatment and/or prevention of disorders or diseases which are at least in part mediated via VR1 receptors and/or CB1 receptors, for the treatment of pain, in particular of neuropathic pain and/or cluster headaches, for the prevention and/or treatment of migraine, peripheral neuropathies, diabetic neuropathies, stroke, AIDS dementia, neurodegenerative diseases, preferably selected from the group consisting of Parkinson's disease, Huntington's chorea, Alzheimer's disease and multiple sclerosis, Lewy body disease, brain injuries, nerve injuries, motor neurone diseases, convulsions in epilepsy, emesis, disorders of food intake, preferably selected from the group consisting of bulimia, anorexia, cachexia and obesity, high blood pressure, depression, glaucoma, urinary incontinence, bladder hyperactivity, diseases caused by prions, infectious rhinitis and/or interstitial cystitis.

The pharmaceutical preparations according to the invention are particularly suitable for the treatment of pain, preferably of neuropathic pain and/or cluster headaches.

The present invention also provides the use of at least one substituted imidazo[1,2-a]pyridine compound according to the invention corresponding to formula I, optionally in the form of one of the pure stereoisomers thereof, in particular enantiomers or diastereomers, the racemate thereof or in the form of mixtures of the stereoisomers, in particular the enantiomers or diastereomers, in any desired mixing ratio, or in each case in the form of a corresponding salt or in the form of a corresponding solvate, for the production of a pharmaceutical preparation for vanilloid receptor 1 (VR1) regulation, for cannabinoid receptor 1 (CB1) regulation, for the treatment and/or prevention of disorders or diseases which are at least in part mediated via VR1 receptors and/or CB1 receptors, for the treatment of pain, in particular of neuropathic pain and/or cluster headaches, for the prevention and/or treatment of migraine, peripheral neuropathies, diabetic neuropathies, stroke, AIDS dementia, neurodegenerative diseases, preferably selected from the group consisting of Parkinson's disease, Huntington's chorea, Alzheimer's disease and multiple sclerosis, Lewy body disease, brain injuries, nerve injuries, motor neurone diseases, of convulsions in epilepsy, emesis, disorders of food intake, preferably selected from the group consisting of bulimia, anorexia, cachexia and obesity, high blood pressure, depression, glaucoma, urinary incontinence, bladder hyperactivity, diseases caused by prions, infectious rhinitis and/or interstitial cystitis.

It has moreover surprisingly been found that substituted imidazo[1,2-a]pyridine compounds corresponding to formula Ia stated below and optionally in each case the stereoisomers, corresponding salts and corresponding solvates thereof likewise exhibit an affinity for vanilloid receptor subtype 1 (VR1) or for cannabinoid receptor 1 (CB1).

The present invention accordingly also provides the use of at least one substituted imidazo[1,2-a]pyridine compound corresponding to formula Ia,

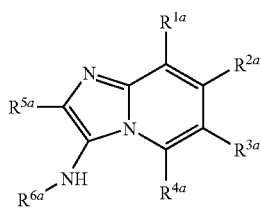

(Ia)

in which
$R^{1a}$, $R^{2a}$, $R^{3a}$ and $R^{4a}$ may be identical or different and respectively denote hydrogen, halogen, a hydroxy group, a cyano group, a nitro group, an amino group, a carboxy group, a —C(=O)—$R^{7a}$ group, a —(C=O)—$OR^{8a}$ group, an $OR^{9a}$ group, a linear or branched, saturated or unsaturated, optionally at least monosubstituted aliphatic residue, a saturated or unsaturated, optionally at least monosubstituted cycloaliphatic residue optionally attached via an alkylene group, or two adjacent residues $R^{1a}$ and $R^{2a}$, $R^{2a}$ and $R^{3a}$ or $R^{3a}$ and $R^{4a}$ in each case together form a 3- or 4-membered, saturated or unsaturated, aliphatic chain optionally comprising at least one heteroatom as a chain link, and the respective remaining residues $R^{3a}$ and $R^{4a}$, $R^{1a}$ and $R^{4a}$ or $R^{1a}$ and $R^{2a}$ denote hydrogen, $R^{5a}$ denotes a linear or branched, saturated or unsaturated, optionally at least monosubstituted aliphatic residue, a saturated or unsaturated, optionally at least monosubstituted cycloaliphatic residue optionally comprising at least one heteroatom as a ring member, which cycloaliphatic residue is optionally attached via an alkylene group and may be fused with an optionally at least monosubstituted, mono- or polycyclic ring system, or an optionally at least monosubstituted aryl or heteroaryl residue optionally attached via an alkylene group, which aryl or heteroaryl residue may be fused with an optionally at least monosubstituted, mono- or polycyclic ring system, $R^{6a}$ denotes a linear or branched, saturated or unsaturated, optionally at least monosubstituted aliphatic residue with 1 to 12 carbon atoms, $R^{7a}$ denotes a linear or branched, saturated or unsaturated, optionally at least monosubstituted aliphatic residue, a saturated or unsaturated, optionally at least monosubstituted cycloaliphatic residue optionally comprising at least one heteroatom as a ring member, which cycloaliphatic residue is optionally attached via an alkylene group and may be fused with an optionally at least monosubstituted, mono- or polycyclic ring system, or an optionally at least monosubstituted aryl or heteroaryl residue optionally attached via an alkylene group, which aryl or heteroaryl residue may be fused with an optionally at least monosubstituted, mono- or polycyclic ring system, $R^{8a}$ denotes a linear or branched, saturated or unsaturated, optionally at least monosubstituted aliphatic residue, a saturated or unsaturated, optionally at least monosubstituted cycloaliphatic residue optionally comprising at least one heteroatom as a ring member, which cycloaliphatic residue is optionally attached via an alkylene group and may be fused with an optionally at least monosubstituted, mono- or polycyclic ring system, or an optionally at least monosubstituted aryl or heteroaryl residue optionally attached via an alkylene group, which aryl or heteroaryl residue may be fused with an optionally at least monosubstituted, mono- or polycyclic ring system, $R^{9a}$ denotes a linear or branched, saturated or unsaturated, optionally at least monosubstituted aliphatic residue, a saturated or unsaturated, optionally at least monosubstituted cycloaliphatic residue optionally comprising at least one heteroatom as a ring member, which cycloaliphatic residue is optionally attached via an alkylene group and may be fused with an optionally at least monosubstituted, mono- or polycyclic ring system, or an optionally at least monosubstituted aryl or heteroaryl residue optionally attached via an alkylene group, which aryl or heteroaryl residue may be fused with an optionally at least monosubstituted, mono- or polycyclic ring system, optionally in the form of the pure stereoisomers thereof, in particular enantiomers or diastereomers, the racemates thereof or in the form of mixtures of the stereoisomers, in particular the enantiomers and/or diastereomers, in any desired mixing ratio, or in each case in the form of corresponding physiologically acceptable salts or in each case in the form of corresponding physiologically acceptable solvates, for the production of a pharmaceutical preparation for VR1 receptor regulation, for CB1 receptor regulation, for the treatment and/or prevention of disorders or diseases which are at least in part mediated via VR1 receptors and/or CB1 receptors, for the treatment of neuropathic pain, for the treatment of cluster headaches, for the prevention and/or treatment of one or more diseases selected from the group consisting of peripheral neuropathies, diabetic neuropathies, stroke, AIDS dementia, Lewy body disease, brain injuries, nerve injuries, motor neurone diseases, convulsions in epilepsy, emesis, disorders of food intake, preferably selected from the group consisting of bulimia, cachexia, anorexia and obesity, depression, glaucoma, urinary incontinence, bladder hyperactivity, diseases caused by prions, infectious rhinitis and interstitial cystitis.

If one or more of the residues $R^{1a}$-$R^{9a}$ denote a linear or branched, saturated or unsaturated aliphatic residue, which is mono- or polysubstituted, for example with 1, 2, 3, 4 or 5 substituents, the substituents thereof may in each case mutually independently preferably be selected from the group consisting of $C_{1-4}$ alkoxy, hydroxy, halogen, —$CHF_2$, —$CH_2F$, —$CF_3$, phenyl, phenoxy, cyano, nitro, amino and di-($C_{1-3}$)-alkylamino, particularly preferably from the group consisting of methoxy, ethoxy, n-propoxy, n-butoxy, tert.-butoxy, hydroxy, F, Cl, Br, —$CHF_2$, —$CH_2F$, —$CF_3$, phenyl, phenoxy, cyano, nitro, amino, dimethylamino and diethylamino.

Suitable saturated or unsaturated aliphatic residues, i.e. alkyl, alkenyl and alkynyl residues, which may be mono- or polysubstituted, for example with 1, 2, 3, 4 or 5 substituents, include, for example, methyl, ethyl, n-propyl, iso-propyl, n-butyl, iso-butyl, sec-butyl, tert.-butyl, n-pentyl, iso-pentyl, neopentyl, n-hexyl, 2-hexyl, n-heptyl, n-octyl, 1,1,3,3-tetramethylbutyl, n-nonyl, n-decyl, n-uncedyl, n-dodecyl, vinyl, propenyl, propynyl, butenyl, butynyl, pentenyl, pentynyl, hexenyl, hexynyl, octenyl or octynyl.

If one or more of the residues $R^{1a}$-$R^{5a}$ and $R^{7a}$-$R^{9a}$ denote a saturated or unsaturated cycloaliphatic residue optionally attached via an alkylene group and optionally comprising at least one heteroatom as a ring member, which cycloaliphatic residue is mono- or polysubstituted, for example with 1, 2, 3, 4, or 5 substituents, the substituents thereof may, in each case mutually independently, preferably be selected from the group consisting of $C_{1-4}$ alkyl, $C_{1-4}$ alkoxy, hydroxy, halogen, —$CHF_2$, —$CH_2F$, —$CF_3$, phenyl, phenoxy, cyano, nitro, amino and di-($C_{1-3}$)-alkylamino, particularly preferably from the group consisting of methyl, ethyl, n-propyl, iso-propyl, n-butyl, sec-butyl, tert.-butyl, methoxy, ethoxy, propoxy, butoxy, tert.-butoxy, hydroxy, F, Cl, Br, —$CHF_2$, —$CH_2F$, —$CF_3$, phenyl, phenoxy, cyano, nitro, amino, dimethylamino and diethylamino.

Suitable cycloaliphatic residues, which may be mono- or polysubstituted, for example with 1, 2, 3, 4 or 5 substituents, include, for example, cyclopropyl, cyclobutyl, cyclopentyl, cyclohexyl, cycloheptyl, cyclooctyl, cyclopentenyl, cyclohexenyl, cycloheptenyl, cyclooctenyl, imidazolidinyl, tetrahydrofuranyl (tetrahydrofuryl), piperidinyl, piperazinyl or morpholinyl.

If one or more of the residues $R^{5a}$ and $R^{7a}$-$R^{9a}$ denote an aryl or heteroaryl residue optionally attached via an alkylene group, which aryl or heteroaryl residue is mono- or polysubstituted, for example with 1, 2, 3, 4, or 5 substituents, the substituents thereof may, in each case mutually independently, preferably be selected from the group consisting of $C_{1-4}$ alkoxy, $C_{1-4}$ alkyl, hydroxy, halogen, —$CHF_2$, —$CH_2F$, —$CF_3$, phenyl, phenoxy, cyano, nitro, amino and di-($C_{1-3}$)-alkylamino, particularly preferably from the group consisting of methyl, ethyl, n-propyl, iso-propyl, n-butyl, sec-butyl, tert.-butyl, methoxy, ethoxy, n-propoxy, n-butoxy, tert.-butoxy, hydroxy, F, Cl, Br, —$CHF_2$, —$CH_2F$, —$CF_3$, phenyl, phenoxy, cyano, nitro, amino, dimethylamino and diethylamino. Examples of suitable aryl residues include phenyl, 1-naphthyl and 2-naphthyl. Suitable heteroaryl residues include, for example, pyrrolyl, indolyl, furyl (furanyl), benzo[b]furanyl, thienyl (thiophenyl), benzo[b]thienyl, pyrazolyl, imidazolyl, thiazolyl, thiadiazolyl, triazolyl, oxazolyl, isoxazolyl, pyridinyl, pyridazinyl, pyrimidinyl, pyrazinyl, pyranyl, indazolyl, purinyl, indolizinyl, quinolinyl, isoquinolinyl and quinazolinyl.

Suitable 5- or 6-membered heteroaryl residues, in particular, include pyrrolyl, furyl (furanyl), thienyl (thiophenyl), pyrazolyl, imidazolyl, thiazolyl, thiadiazolyl, triazolyl, oxazolyl, isoxazolyl, pyridinyl, pyridazinyl, pyrimidinyl, pyrazinyl and pyranyl.

If one or more of the residues $R^{5a}$ and $R^{7a}$-$R^{9a}$ denote a cycloaliphatic residue or comprise a cycloaliphatic residue which contains one or more, for example 1, 2 or 3 heteroatoms as ring member(s), said heteroatoms may, mutually independently, preferably be selected from the group consisting of sulfur, oxygen and nitrogen.

If one or more of the residues $R^{5a}$ and $R^{7a}$-$R^{9a}$ denote a heteroaryl residue or comprise a heteroaryl residue, the heteroatoms may, mutually independently, preferably be selected from the group consisting of sulfur, oxygen and nitrogen. The heteroaryl residue may preferably optionally comprise 1, 2, 3, 4 or 5 heteroatom(s) as ring member(s).

If two adjacent residues $R^{1a}$ and $R^{2a}$, $R^{2a}$ and $R^{3a}$ or $R^{3a}$ and $R^{4a}$, respectively, together form a 3- or 4-membered, saturated or unsaturated aliphatic chain which comprises one or more, for example 1 or 2, heteroatoms as chain link(s), said heteroatoms may, mutually independently, preferably be selected from the group consisting of sulfur, oxygen and nitrogen.

Suitable chains which may be mentioned include, for example, —CH=$CH_2$—$CH_2$—, —$CH_2$—$CH_2$—$CH_2$—, —$CH_2$—$CH_2$—$CH_2$—$CH_2$—, —O—$CH_2$—O—, —NH—$CH_2$—$CH_2$—O—, —O—$CH_2$—$CH_2$—O—, —NH—$CH_2$—$CH_2$—S— and —S—$CH_2$—$CH_2$—S—.

Persons skilled in the art will understand that if two adjacent residues $R^{1a}$ and $R^{2a}$, $R^{2a}$ and $R^{3a}$ or $R^{3a}$ and $R^{4a}$, respectively, together form a 3- or 4-membered, saturated or unsaturated, aliphatic chain optionally comprising at least one heteroatom as a chain link, this gives rise to a tricyclic ring system.

If one or more of the residues $R^{1a}$ to $R^{5a}$ and $R^{7a}$ to $R^{9a}$ comprise a linear or branched $C_{1-5}$ alkylene group, this may preferably be selected from the group consisting of —($CH_2$)—, —($CH_2$)$_2$—, —C(H)($CH_3$)—, —C($CH_3$)$_2$—, —($CH_2$)$_3$—, —($CH_2$)$_4$—, —($CH_2$)$_5$—, —C(H)(C(H)($CH_3$)$_2$)— and —C(C$_2$H$_5$)(H)—.

It is preferred to use those substituted imidazo[1,2-a]pyridine compounds corresponding to formula (Ia) in which $R^{1a}$, $R^{2a}$, $R^{3a}$ and $R^{4a}$ may be identical or different and respectively denote hydrogen, F, Cl, Br, a hydroxy group, a cyano group, a nitro group, an amino group, a carboxy group, a —C(=O)—$R^{7a}$ group, a —C(=O)—$OR^{8a}$ group, an $OR^{9a}$ group, a linear or branched, saturated or unsaturated, optionally at least monosubstituted aliphatic $C_{1-12}$ residue, a saturated or unsaturated, optionally at least monosubstituted cycloaliphatic $C_{3-8}$ residue optionally attached via a $C_{1-8}$ alkylene group, or two adjacent residues $R^{1a}$ and $R^{2a}$, $R^{2a}$ and $R^{3a}$ or $R^{3a}$ and $R^{4a}$, respectively, together form a 3- or 4-membered, saturated or unsaturated, aliphatic chain link optionally comprising at least one heteroatom as a chain link, and the respective remaining residues $R^{3a}$ and $R^{4a}$, $R^{1a}$ and $R^{4a}$ or $R^{1a}$ and $R^{2a}$ denote hydrogen, preferably hydrogen, F, Cl, Br, a hydroxy group, a carboxy group, a —C(=O)—$R^{7a}$ group, a —(C=O)—$OR^{8a}$ group, an $OR^{9a}$ group or a linear or branched $C_{1-12}$ alkyl residue, particularly preferably hydrogen, F, Cl or a linear or branched $C_{1-4}$ alkyl residue, very particularly preferably H, Cl or a methyl group, and the respective remaining residues $R^{5a}$ to $R^{9a}$ have the above-stated meaning, in each case optionally in the form of the pure stereoisomers thereof, in particular enantiomers or diastereomers, the racemates thereof or in the form of mixtures of the stereoisomers, in particular the enantiomers or diastereomers, in any desired mixing ratio, or in each case in the form of corresponding salts or in each case in the form of corresponding solvates.

It is further preferred to use those substituted imidazo[1,2-a]pyridine compounds corresponding to formula (Ia) in which $R^{5a}$ denotes a linear or branched, saturated or unsaturated, optionally at least monosubstituted aliphatic $C_{1-12}$ residue, a saturated or unsaturated, optionally at least monosubstituted cycloaliphatic $C_{3-8}$ residue optionally comprising at least one heteroatom as a ring member, which cycloaliphatic residue is optionally attached via a $C_{1-8}$ alkylene group and may be fused with an optionally at least monosubstituted, mono- or polycyclic ring system, or an optionally at least monosubstituted, 5- or 6-membered aryl or heteroaryl residue optionally attached via a $C_{1-8}$ alkylene group, which aryl or heteroaryl residue may be fused with an optionally at least monosubstituted, mono- or polycyclic ring system, preferably a linear or branched $C_{1-8}$ alkyl residue, a saturated or unsaturated, optionally at least monosubstituted cycloaliphatic $C_{3-8}$ residue optionally comprising at least one heteroatom as a ring member, which cycloaliphatic residue is optionally attached via a $C_{1-3}$ alkylene group, or an optionally at least monosubstituted, 5- or 6-membered aryl or heteroaryl residue optionally attached via a $C_{1-3}$ alkylene group, particularly preferably a residue selected from the group consisting of optionally at least monosubstituted phenyl, optionally at least monosubstituted furyl, optionally at least monosubstituted thienyl and optionally at least monosubstituted pyridyl, very particularly preferably a 2-furyl, 3-furyl, 2-thienyl, 3-thienyl, 2-pyridyl, 3-pyridyl, 4-pyridyl or phenyl residue, and the respective remaining residues $R^{1a}$ to $R^{4a}$ and $R^{6a}$ to $R^{9a}$ have the above-stated meaning, in each case optionally in the form of the pure stereoisomers thereof, in particular enantiomers or diastereomers, the racemates thereof or in the form of mixtures of the stereoisomers, in particular the enantiomers or diastereomers, in any desired mixing ratio, or in each case in the form of corresponding salts or in each case in the form of corresponding solvates.

It is furthermore preferred to use those substituted imidazo[1,2-a]pyridine compounds corresponding to formula (Ia), in which $R^{6a}$ denotes a linear or branched, optionally at least monosubstituted $C_{1-12}$ alkyl residue, particularly preferably a linear $C_{1-12}$ alkyl residue, a —$CH_2$-phenyl group, a —$C(CH_3)_2$—$(CH_2)_{0-8}$—$CH_3$ group or a 1,1,3,3-tetramethyl-butyl-group, very particularly preferably a —$(CH_2)_6$—$CH_3$ group, a —$(CH_2)_7$—$CH_3$ group, a —$(CH_2)_8$—$CH_3$ group, —$CH_2$-phenyl-group, a —$C(CH_3)_2$—$(CH_2)_4$—$CH_3$ group, a —$C(CH_3)_2$—$(CH_2)_5$—$CH_3$ group, a —$C(CH_3)_2$—$(CH_2)_6$—$CH_3$ group or a 1,1,3,3-tetramethylbutyl group, and in each case the residues $R^{1a}$ to $R^{5a}$ and $R^{7a}$ to $R^{9a}$ have the above-stated meaning, in each case optionally in the form of the pure stereoisomers thereof, in particular enantiomers or diastereomers, the racemates thereof or in the form of mixtures of the stereoisomers, in particular the enantiomers or diastereomers, in any desired mixing ratio, or in each case in the form of corresponding salts or in each case in the form of corresponding solvates.

It is also preferred to use those substituted imidazo[1,2-a]pyridine compounds corresponding to formula (Ia) are in which the residue $R^{7a}$ denotes a linear or branched, saturated or unsaturated, optionally at least monosubstituted aliphatic $C_{1-8}$ residue, a saturated or unsaturated, optionally at least monosubstituted cycloaliphatic $C_{3-8}$ residue optionally comprising at least one heteroatom as a ring member, which cycloaliphatic residue is optionally attached via a $C_{1-8}$ alkylene group and may be fused with an optionally at least monosubstituted, mono- or polycyclic ring system, or an optionally at least monosubstituted, 5- or 6-membered aryl or heteroaryl residue optionally attached via a $C_{1-8}$ alkylene group, which aryl or heteroaryl residue may be fused with an optionally at least monosubstituted, mono- or polycyclic ring system, preferably a linear or branched $C_{1-4}$ alkyl residue, a saturated or unsaturated, optionally at least monosubstituted cycloaliphatic $C_{3-8}$ residue optionally comprising at least one heteroatom as a ring member, which cycloaliphatic residue is optionally attached via a $C_{1-3}$ alkylene group, or denotes an optionally at least monosubstituted, 5- or 6-membered aryl or heteroaryl residue optionally attached via a $C_{1-3}$ alkylene group, which aryl or heteroaryl residue may be fused with an optionally at least monosubstituted, mono- or polycyclic ring system, and the respective remaining residues $R^{1a}$ to $R^{6a}$, $R^{8a}$ and $R^{9a}$ have the above-stated meaning in each case optionally in the form of the pure stereoisomers thereof, in particular enantiomers or diastereomers, the racemates thereof or in the form of mixtures of the stereoisomers, in particular the enantiomers or diastereomers, in any desired mixing ratio, or in each case in the form of corresponding salts or in each case in the form of corresponding solvates.

It is likewise preferred to use those substituted imidazo[1,2-a]pyridine compounds corresponding to formula (Ia) in which the residue $R^{8a}$ denotes a linear or branched, saturated or unsaturated, optionally at least monosubstituted aliphatic $C_{1-8}$ residue, a saturated or unsaturated, optionally at least monosubstituted cycloaliphatic $C_{3-8}$ residue optionally comprising at least one heteroatom as a ring member, which cycloaliphatic residue is optionally attached via a $C_{1-8}$ alkylene group and may be fused with an optionally at least monosubstituted, mono- or polycyclic ring system, or an optionally at least monosubstituted, 5- or 6-membered aryl or heteroaryl residue optionally attached via a $C_{1-8}$ alkylene group, which aryl or heteroaryl residue may be fused with an optionally at least monosubstituted, mono- or polycyclic ring system, preferably a linear or branched $C_{1-4}$ alkyl residue, a saturated or unsaturated, optionally at least monosubstituted cycloaliphatic $C_{3-8}$ residue optionally comprising at least one heteroatom as a ring member, which cycloaliphatic residue is optionally attached via a $C_{1-3}$ alkylene group, or an optionally at least monosubstituted, 5- or 6-membered aryl or heteroaryl residue optionally attached via a $C_{1-3}$ alkylene group, which aryl or heteroaryl residue may be fused with an optionally at least monosubstituted, mono- or polycyclic ring system, and the respective remaining residues $R^{1a}$ to $R^{7a}$ and $R^{9a}$ have the above-stated meaning, in each case optionally in the form of the pure stereoisomers thereof, in particular enantiomers or diastereomers, the racemates thereof or in the form of mixtures of the stereoisomers, in particular the enantiomers or diastereomers, in any desired mixing ratio, or in each case in the form of corresponding salts or in each case in the form of corresponding solvates.

It is further preferred to use those substituted imidazo[1,2-a]pyridine compounds corresponding to formula (Ia) in which the residue $R^{9a}$ denotes a linear or branched, saturated or unsaturated, optionally at least monosubstituted aliphatic $C_{1-8}$ residue, a saturated or unsaturated, optionally at least monosubstituted cycloaliphatic $C_{3-8}$ residue optionally comprising at least one heteroatom as a ring member, which cycloaliphatic residue is optionally attached via a $C_{1-8}$ alkylene group and may be fused with an optionally at least monosubstituted, mono- or polycyclic ring system, or an optionally at least monosubstituted, 5- or 6-membered aryl or heteroaryl residue optionally attached via a $C_{1-8}$ alkylene group, which aryl or heteroaryl residue may be fused with an optionally at least monosubstituted, mono- or polycyclic ring system, preferably a linear or branched $C_{1-4}$ alkyl residue, a saturated or unsaturated, optionally-at least monosubstituted cycloaliphatic $C_{3-8}$ residue optionally comprising at least one heteroatom as a ring member, which cycloaliphatic residue is optionally attached via a $C_{1-3}$ alkylene group, or an optionally at least monosubstituted, 5- or 6-membered aryl or heteroaryl residue optionally attached via a $C_{1-3}$ alkylene group, which aryl or heteroaryl residue may be fused with an optionally at least monosubstituted, mono- or polycyclic ring system, and the respective remaining residues $R^{1a}$ to $R^{8a}$ have the above-stated meaning, in each case optionally in the form of the pure stereoisomers thereof, in particular enantiomers or diastereomers, the racemates thereof or in the form of mixtures of the stereoisomers, in particular the enantiomers or diastereomers, in any desired mixing ratio, or in each case in the form of corresponding salts or in each case in the form of corresponding solvates.

It is very particularly preferred to the use one or more substituted imidazo[1,2-a]pyridine compounds corresponding to formula (Ia) selected from the group consisting of:

5,7-dimethyl-2-thiophen-3-yl-imidazo[1,2-a]pyridin-3-yl)-(1,1,3,3-tetramethylbutyl)-amine,
(1,1,3,3-tetramethylbutyl)-(2-thiophen-3-yl-imidazo[1,2-a]pyridin-3-yl)amine,
(7-methyl-2-thiophen-3-yl-imidazo[1,2-a]pyridin-3-yl)-(1,1,3,3-tetramethylbutyl)-amine,
(2-furan-3-yl-imidazo[1,2-a]pyridin-3-yl)-(1,1,3,3-tetramethylbutyl)amine,
(2-furan-3-yl-7-methyl-imidazo[1,2-a]pyridin-3-yl)-(1,1,3,3-tetramethylbutyl)amine,
(2-furan-3-yl-imidazo[1,2-a]pyridine-3-yl)-heptyl-amine,
(1,1-dimethyl-hexyl)-(2-furan-3-yl-imidazo[1,2-a]pyridin-3-yl)-amine,
(1,1-dimethyl-octyl)-(2-furan-3-yl-imidazo[1,2-a]pyridin-3-yl)-amine,
heptyl-(2-thiophen-3-yl-imidazo[1,2-a]pyridin-3-yl)-amine,
(1,1-dimethyl-hexyl)-(2-thiophene-3-yl-imidazo[1,2-a]pyridine-3-yl)-amine,
(2-furan-3-yl-7-methyl-imidazo[1,2-a]pyridin-3-yl)-heptyl-amine,
(2-furan-3-yl-7-methyl-imidazo[1,2-a]pyridin-3-yl)-octyl-amine,
(2-furan-3-yl-7-methyl-imidazo[1,2-a]pyridin-3-yl)-nonyl-amine,
(1,1-dimethyl-hexyl)-(2-furan-3-yl-7-methyl-imidazo[1,2-a]pyridin-3-yl)-amine,
(1,1-dimethyl-heptyl)-(2-furan-3-yl-7-methyl-imidazo[1,2-a]pyridin-3-yl)-amine,
(1,1-dimethyl-octyl)-(2-furan-3-yl-7-methyl-imidazo[1,2-a]pyridin-3-yl)-amine,
(1,1-dimethyl-hexyl)-(7-methyl-2-thiophen-3-yl-imidazo[1,2-a]pyridin-3-yl)-amine,
(1,1-dimethyl-heptyl)-(7-methyl-2-thiophen-3-yl-imidazo[1,2-a]pyridin-3-yl)-amine,
(1,1-dimethyl-octyl)-(7-methyl-2-thiophen-3-yl-imidazo[1,2-a]pyridin-3-yl)-amine,
(7-methyl-2-pyridin-2-yl-imidazo[1,2-a]pyridin-3-yl)-octyl-amine,
(1,1-dimethyl-hexyl)-(7-methyl-2-pyridin-2-yl-imidazo[1,2-a]pyridin-3-yl)-amine,
(1,1-dimethyl-octyl)-(7-methyl-2-pyridin-2-yl-imidazo[1,2-a]pyridin-3-yl)-amine,
(7-methyl-2-pyridine-3-yl-imidazo[1,2-a]pyridin-3-yl)-nonyl-amine,
heptyl-(7-methyl-2-pyridin-4-yl-imidazo[1,2-a]pyridin-3-yl)-amine,
(7-methyl-2-pyridin-4-yl-imidazo[1,2-a]pyridin-3-yl)-octyl-amine,
(1,1-dimethyl-hexyl)-(7-methyl-2-pyridin-4-yl-imidazo[1,2-a]pyridin-3-yl)-amine,
(2-furan-3-yl-6-methyl-imidazo[1,2-a]pyridin-3-yl)-octyl-amine,
(1,1-dimethyl-hexyl)-(2-furan-3-yl-6-methyl-imidazo[1,2-a]pyridin-3-yl)-amine,
(1,1-dimethyl-heptyl)-(6-methyl-2-pyridin-2-yl-imidazo[1,2-a]pyridin-3-yl)-amine,
(1,1-dimethyl-heptyl)-(5-methyl-2-pyridin-2-yl-imidazo[1,2-a]pyridin-3-yl)-amine,
benzyl-(7-methyl-2-thiophen-3-yl-imidazo[1,2-a]pyridin-3-yl)-amine,
(1,1-dimethyl-hexyl)-(7-methyl-2-phenyl-imidazo[1,2-a]pyridin-3-yl)-amine, and
(1,1-dimethyl-hexyl)-(2-furan-3-yl-7-methyl-imidazo[1,2-a]pyridin-3-yl)-amine, and their respective corresponding physiologically acceptable salts and solvates.

The production of the substituted imidazo[1,2-a]pyridine compounds corresponding to formula Ia used according to the invention and optionally the stereoisomers, corresponding physiologically acceptable salts and corresponding physiologically acceptable solvates thereof may in each case proceed in a manner similar to the process stated above for the substituted imidazo[1,2-a]pyridine compounds according to the invention corresponding to formula I, wherein the corresponding starting compounds are likewise commercially obtainable or may be produced using conventional processes known to persons skilled in the art.

Corresponding processes for the production of substituted imidazo[1,2-a]pyridine compounds corresponding to formula Ia are, for example, also described in WO 02/30428 A1, the disclosure of which is hereby incorporated by reference, also in relation to the production of substituted imidazo[1,2-a]pyridine compounds corresponding to formula I.

The pharmaceutical preparations may take the form of liquid, semisolid or solid dosage forms, for example in the form of solutions for injection, drops, succi, syrups, sprays, suspensions, tablets, patches, capsules, dressings, suppositories, ointments, creams, lotions, gels, emulsions, aerosols or in multiparticulate form, for example in the form of pellets or granules, optionally press-moulded into tablets, packaged in capsules or suspended in a liquid, and also be administered as such. The pharmaceutical preparations are suitable for administration to adults and children including small children and babies.

In addition to one or more substituted imidazo[1,2-a]pyridine compounds corresponding to formula I and/or one or more substituted imidazo[1,2-a]pyridine compounds corresponding to formula Ia, in each case optionally in the form of the pure stereoisomers thereof, in particular enantiomers or diastereomers, the racemates thereof or in the form of mixtures of the stereoisomers, in particular the enantiomers or diastereomers, in any desired mixing ratio, or in each case in the form of the acids thereof or the bases thereof or in the form of the physiologically acceptable salts thereof, in particular sodium salts or hydrochloride salts, or in each case in the form of the solvates thereof, in particular hydrates, the pharmaceutical preparations according to the invention conventionally contain further physiologically acceptable pharmaceutical auxiliary substances, which are preferably selected from the group consisting of matrix materials, fillers, solvents, diluents, surface-active substances, dyes, preservatives, disintegrants, slip agents, lubricants, aromas and binders.

Selection of the physiologically acceptable auxiliary substances and the quantities thereof which are to be used depends upon whether the pharmaceutical preparation is to be administered orally, subcutaneously, parenterally, intravenously, intraperitoneally, intradermally, intramuscularly, intranasally, buccally, rectally or topically, for example onto infections of the skin, mucous membranes or eyes. Preparations in the form of tablets, coated tablets, capsules, granules, pellets, drops, succi and syrups are preferred for oral administration, while solutions, suspensions, readily reconstitutible dried preparations and sprays are preferred for parenteral, topical and inhalatory administration. Substituted imidazo[1,2-a]pyridine compounds corresponding to formula I and/or substituted imidazo[1,2-a]pyridine compounds corresponding to formula Ia, in each case optionally in the form of the pure stereoisomers thereof, in particular enantiomers or diastereomers, the racemates thereof or in the form of mixtures of the stereoisomers, in particular the enantiomers or diastereomers, in any desired mixing ratio, or in each case in the form of the acids thereof or the bases thereof or in the form of the physiologically acceptable salts thereof, in particular sodium salts or hydrochloride salts, or in each case in the form of the solvates thereof, in particular hydrates, in a depot in dissolved form or in a dressing, optionally with the addition of skin penetration promoters, are suitable percutaneous administration preparations.

Orally or percutaneously administrable formulations may also release the particular substituted imidazo[1,2-a]pyridine compounds corresponding to formula I and/or the substituted imidazo[1,2-a]pyridine compounds corresponding to formula Ia, optionally in the form of the pure stereoisomers thereof, in particular enantiomers or diastereomers, of the racemates thereof or in the form of mixtures of the stereoisomers, in particular the enantiomers or diastereomers, in any desired mixing ratio, or in each case in the form of the acids thereof or the bases thereof or in the form of the physiologically acceptable salts thereof, in particular sodium salts or hydrochloride salts, or in each case in the form of the solvates thereof, in particular hydrates, in delayed manner.

The production of the pharmaceutical preparations which contain one or more of the substituted imidazo[1,2-a]pyridine compounds corresponding to formula I and/or one or more of the substituted imidazo[1,2-a]pyridine compounds corresponding to formula Ia, proceeds with the assistance of conventional means, devices, methods and processes known to persons skilled in the art, such as are described for example in "Remington's Pharmaceutical Sciences", ed. A. R. Gennaro, 17th ed., Mack Publishing Company, Easton, Pa. (1985), in particular in part 8, chapters 76 to 93, the corresponding disclosure of which is hereby incorporated by reference.

The quantity of the substituted imidazo[1,2-a]pyridine compound(s) to be administered to the patient may vary and is for example dependent on the weight or age of the patient and on the mode of administration, the indication and the severity of the complaint. Conventionally, 0.005 to 5000 mg/kg, preferably 0.05 to 500 mg/kg, particularly preferably 0.05 to 75 mg/kg of patient body weight of at least one such compound are administered.

Pharmacological Test Methods:

(a) Determination of affinity for vanilloid receptor VR1 (capsaicin receptor)

The affinity of the imidazo[1,2-a]-pyridine compounds of the above-stated general formulae I and Ia for vanilloid receptor VR1 (capsaicin receptor) is determined as is described below. This method was developed on the basis of the publication by Acs et al., J. Neurochem. 65, 301-308 (1995). The corresponding description is hereby introduced as a reference and is deemed to be part of the disclosure.

A. Materials:
Sprague Dawley rats weighing between 150-300 g (breeder: Charles River Deutschland, 32699 Extertal, Germany)
HEPES (item no. H-3375, SIGMA)
NaCl (item no. 6400.1000; Merck)
KCl (item no.: 4936.1000; Merck)
HCl (item no.: 1.00317; Merck)
[$^3$H] resiniferatoxin ([$^3$H] RTX) (item no.: NET-1132, Perkin-Elmer)
Resiniferatoxin (RTX, cold) (item no.: 550-179-M001, Alexis)
D-Glucose (item no.: 1.08337.1000, Merck)
Sucrose (item no.: S-9378, Sigma)
$\alpha_1$-acid glycoprotein (item no.: G-3643, Sigma)
BSA (bovine serum albumin, item no.: A-2153, Sigma)
GF/B filter mats (Brandel Inc., cat. no. FP 100, size: 2¼"×12¼")
Ready Protein scintillating material (item no. 586604 Beckman)

Buffer: (Concentration values in brackets in each case in mM)
HEPES (10); KCl (5); NaCl (5.8); CaCl (0.75); MgCl (2.0); D-glucose (12);
sucrose (137). The pH value is adjusted at room temperature using 20% strength HCl.

B. Preparation of Membranes

The cervical region and one third of the following thoracic region is isolated from the spinal cord of male Sprague Dawley rats (breeder: Charles River Deutschland, 32699 Extertal) and used for preparation of the membrane. After the combined tissue is weighed, it is homogenized in ice-cooled buffer of the above-stated composition. 20 ml of buffer were used per 1 g of tissue (1:20 weight/volume). Homogenisation performed with a homogeniser from Kinematica, model Polytron PT-3000 with PT-DA-3012/2 drive unit. The spinal cord tissue is disrupted within 60 seconds in the cold buffer with ice cooling at a rotational speed of 6000 rpm. The material is then centrifuged for 10 minutes at 1000 g and +4° C. and the resultant precipitate discarded. The supernatant is resuspended in the same volume of buffer of the above-stated composition. The material is then centrifuged for 40 minutes at 48,000 g and +4° C. and the supernatant discarded. The resultant precipitate is resuspended in 30 ml of buffer of the above-stated composition and used in this form in the vanilloid receptor (VR1) assay.

C. Incubation Batch:

| Substance | μl | mg protein in batch | Concentration in batch |
|---|---|---|---|
| Ligand: [$^3$H] RTX | 10 | — | 100 pM |
| Homogenate | 600 | approx. 2.5–3.0 | |
| BSA | 100 | 0.25 mg/ml | |
| Substance under investigation | 20 | | variable |
| NSB* value (with cold RTX instead of substance under investigation) | | | 0.1 μM |
| Buffer to 1000 μl | 270 | | |

NSB* = nonspecific binding

Incubation is performed in the water bath for one hour at 37° C. The samples are then placed in an ice bath for 15 minutes. In order to minimise nonspecific adsorption of the RTX, 100 μg of $α_1$-acid glycoprotein (in 50 μl of buffer) are added to each incubation tube. The samples are then thoroughly mixed on a vortex shaker and left to stand for 10 minutes. The batches are then filtered with the assistance of the model M-24R "Brandel Cell Harvester" through a GF/B glass fiber filter mat which has been presoftened in tris buffer. The filter is then rinsed through 3 times with 4 ml portions of ice-cold HEPES buffer of the above-stated composition for each sample. The filters are transferred into scintillation counter vessels, each is combined with a 10 ml portion of "Ready Protein" scintillating material, and the vessels are closed with screw caps. The vessels are shaken on the vortex shaker and left to stand for at least 15 hours in the fume cupboard. The samples are then measured on the β-counter (model 1409 Wallac, Perkin Elmer, 63110 Rogau-Jügesheim, Germany).

(b) Functional Investigations on Vanilloid Receptor (VR1)

The agonistic or antagonistic action of the substances to be investigated on the vanilloid receptor (VR1) may be determined with the following assay. According to this assay, the influx of $Ca^{2+}$ through the channel is quantified with the assistance of a $Ca^{2+}$-sensitive dye (type Fluo4, Molecular Probes Europe BV, Leiden, Netherlands) in a Fluorescent Imaging Plate Reader (FLIPR, Molecular Devices, Sunnyvale, USA).

Method:

Chinese hamster ovary cells (CHO K1 cells, European Collection of Cell Cultures (ECACC), Great Britain) are stably transfected with the VR1 gene. For functional investigations, these cells are plated out onto poly-D-lysine-coated, black 96 well plates with a clear bottom (BD Biosciences, Heidelberg, Germany) at a density of 25,000 cells/well. The cells are incubated overnight at 37° C. and 5% $CO_2$ in a culture medium (Ham's Nutrient Mixture F12, 10 vol. % FCS (foetal calf serum), 18 μg/mL L-proline). On the following day, the cells are incubated with Fluo4 (Fluo4 2 μM, Pluronic F127 0.01 vol. %, Molecular Probes in HBSS (Hank's buffered saline solution), Gibco Invitrogen GmbH, Karlsruhe, Germany) for 30 minutes at 37° C. The plates are then washed 3 times with HBSS buffer and, after a further 15 minutes' incubation at room temperature, used for $Ca^{2+}$ measurement in the FLIPR. $Ca^{2+}$-dependent fluorescence is here measured before and after addition of the substances to be investigated (wavelength $λ_{ex}$=488 nm, $λ_{em}$=540 nm). Quantification proceeds by measuring the highest fluorescence intensity (FC, fluorescence counts) over time.

FLIPR assay:

The FLIPR protocol comprises 2 additions of substance. The substances to be tested (10 μM) are firstly pipetted onto the cells and $Ca^{2+}$ influx is compared with the control (capsaicin 10 μM) (% activation relative to the $Ca^{2+}$ signal after addition of 10 μM of capsaicin). After 5 minutes' incubation, 100 nM of capsaicin are added and the influx of $Ca^{2+}$ is again determined. Desensitising agonists and antagonists resulted in suppression of $Ca^{2+}$ influx. The percentage inhibition in comparison with the maximum achievable inhibition with 10 μM capsazepine is calculated.

(c) Determination of Affinity for Cannabinoid Receptor 1 (CB1)

The affinity of the imidazo[1,2-a]pyridine compounds corresponding to formulas I and Ia for cannabinoid receptor (CB1) is determined as described below. The method was developed on the basis of the publication of D'Ambra et al, J. Med. Chem. 35, 124-135 (1992), but at variance therewith the ligand stated below is used. The disclosure of this article is hereby incorporated by reference.

A. Materials:

Sprague Dawley rats weighing between 150-350 g (breeder: Charles River Deutschland, 32699 Extertal, Germany)
Ligand: [$^3$H] WIN55, 212-2; Perkin Elmer, item. no. NET 1058
Ligand cold: WIN 55, 212-2 mesylate; Tocris; item. no. 1038
HEPES: Sigma, item no. H-3375
BSA: Sigma, item no. A-2153
GF/B filter mats (Brandel Inc., cat. no. FP 100, size 2¼"× 12¼")
Ready Protein scintillating material (item no. 586604, Beckmann, 85716 Unterschleißheim)
Tissue: rat cerebellum
Tissue & incubation buffer: 20 mM HEPES pH 7.0.
Filtration buffer: 20 mM HEPES pH 7.0 containing 0.5 mg of BSA/ml which prevents adsorption.
Filter mat softening buffer: 20 mM HEPES pH 7.0 containing 5 mg of BSA/ml.

B. Preparation of Cerebellum:

20 ml of ice-cooled buffer are used per 1 g of brain tissue. The brain tissue is disrupted within 30 seconds in the cold buffer with ice cooling at a rotational speed of 6000 rpm using a homogeniser from Kinematica, model Polytron PT-3000 with PT-DA-3012/2 drive unit. The resultant homogenate is then diluted with cold buffer to a ratio of 100 ml/g of tissue. Centrifugation is then performed for 15 minutes at 49,000 g and 4° C. Once centrifugation is complete, the supernatants are decanted and the precipitates resuspended in fresh, cold buffer. Acceptable suspension of the pellets is obtained at only 1000 rpm in the homogeniser with ice cooling and a processing time of at most 60 seconds. This last centrifugation step is repeated twice more (in each case washed with 20 mM HEPES pH 7.0). The precipitated is then suspended with buffer in a ratio of 1:120 (weight/volume).

C. Incubation:

| Substances | | M | μl |
|---|---|---|---|
| Buffer | (20 mM HEPES, pH 7.0) | | 190 |
| Ligand | WIN 55.212-2 | 0.5 nM | 10 |
| BSA | | 1 mg/batch | 100 |
| Test substance (or NSB*) | variable (1 × $10^{-6}$ M WIN 55.212-2) | $10^{-4}$–$10^{-10}$ M | 100 |
| Membranes | in HEPES-P. pH 7.0 | >100 μg protein | 600 |

*nonspecific binding

Incubation is performed for 90 minutes at room temperature, i.e. 25° C. The batches are then rapidly suction filtered with the assistance of the Brandel Cell Harvester (model M-24-R, Adi Hassel, 80809 Munich, Germany) through GF/B filter mats, which have previously been softened in HEPES buffer pH 7.0 containing 5 mg/ml of BSA, and rewashed with 20 ml of filtration buffer (ice-cooled). After transferring the filters into scintillation vials and adding a 10 ml portion of scintillation liquid (Ready Protein) to each and then leaving to stand for 15 hours, the samples are measured in the scintillation counter (Perkin Elmer, model Wallac 1409).

EXAMPLES

The invention will be explained hereinafter with reference to illustrative examples, which are given merely as examples and are not intended to restrict the overall scope of the invention. The chemicals and solvents used were purchased from commercial sources. (Acros, Aldrich, Chempur, Fluka, Lancaster and Merck). The NMR spectra were measured with spectrometers made by Bruker Analytik GmbH, Silberstreifen 4, D-76287 Rheinstetten. The instrument names are as follows: for 300 MHz: Avance DPX 300 MHz, for 600 MHz: Avance DRX 600 MHz. The ESI mass spectra were measured with a Finnigan LCQ model instrument made by Thermoquest (Analytische Systeme GmbH, Boschring 12, D-63329 Egelsbach).

Example 1

(5,7-Dimethyl-2-thiophen-3-yl-imidazo[1,2-a]pyridin-3-yl)-(1,1,3,3-tetramethylbutyl)-amine hydrochloride 2.82 g (23.0 mmol) of 2-amino4,6-dimethylpyridine were dissolved in 40 ml of dichloromethane, 1.5 mol equivalents (3.37 g; 30.1 mmol) of thiophene-3-carbaldehyde, one mol equivalent of 2-isocyano-2,4,4-trimethylpentane (2.79 g; 20.0 mmol) and 2 ml of aqueous perchloric acid (20 wt. % strength) were added and the resultant reaction mixture stirred overnight at room temperature. The mixture was worked up by adding 50 ml of saturated sodium chloride solution and 50 ml of dichloromethane, separating the phases and extracting the aqueous phases twice more with 30 ml portions of dichloromethane. The combined organic phases were washed in succession with 40 ml of buffer solution (pH 10) and 40 ml of saturated sodium chloride solution, dried over sodium sulfate, filtered, evaporated in a rotary evaporator under reduced pressure and solvent residues were stripped out under an oil pump vacuum. The resulting crude product, 8.07 g of a yellow oil, was heated to reflux in 50 ml of hexane. After cooling with stirring, the suspended solid was filtered out and dried under reduced pressure, 3.22 g of solid being obtained. A yellow oil (4.76 g) was isolated from the filtrate by evaporation under reduced pressure. The solid was dissolved in 25 ml of 2-butanone and combined with ice cooling with 89 µl of water and 1.25 ml of chlorotrimethylsilane. After stirring overnight, the resultant hydrochloride of (5,7-dimethyl-2-thiophen-3-yl-imidazo-[1,2-a]pyridin-3-yl)-(1,1,3,3-tetramethylbutyl)amine was filtered out and dried (yield: 2.32 g). In addition, the likewise isolated oil was subjected to similar hydrochloride precipitation and the resultant solid (4.05 g) was reconverted in dichloromethane into the base (3.75 g) with 2M sodium hydroxide solution and the base was redissolved in boiling hexane (100 ml). The solid formed on cooling was filtered out (2.43 g) and, as described above, converted with chlorotrimethylsilane in aqueous 2-butanone into the corresponding hydrochloride (2.56 g). In total, 4.88 g of (5,7-dimethyl-2-thiophen-3-yl-imidazo[1,2-a]pyridin-3-yl)-(1,1,3,3-tetramethylbutyl)amine hydrochloride were obtained.

$^1$H-NMR (600 MHz, CDCl$_3$): δ=0.88 (s, 15H); 1.43 (s, 2 H); 2.48 (s, 3H); 3.06 (s, 3H); 3.33 (br. s, 2 H); 7.11 (s, 1 H); 7.54 (s, 1 H); 7.76 (s, 2 H); 8.31 (s, 1 H).

Example 2

(1,1,3,3-Tetramethylbutyl)-(2-thiophen-3-yl-imidazo-[1,2-a]pyridin-3-yl)amine hydrochloride As described for Example 1, 9.99 g of crude product were obtained from 3.11 g (33.0 mmol) of 2-aminopyridine, 4.83 g (43.1 mmol) of thiophene-3-carbaldehyde, 4.00 g (28.7 mmol) of 2-isocyano-2,4,4trimethylpentane(1,1,3,3-tetramethyl-butylisonitrile) and 2.8 ml of aqueous perchloric acid (20 wt. % strength) in 60 ml of dichloromethane. The crude product was heated to reflux in 150 ml of hexane, after cooling with stirring the suspended solid was filtered out and dried under reduced pressure (7.85 g). 1.5 g of this solid were dissolved in 12 ml of 2-butanone and combined with ice cooling with 45 µl of water and 0.64 ml of chlorotrimethylsilane. After stirring overnight, the resultant hydrochloride of (1,1,3,3-tetramethyl-butyl)-(2-thiophen-3-yl-imidazo[1,2-a]pyridin-3-yl)amine was filtered out and dried (yield 1.67 g).

$^1$H-NMR (600 MHz, CDCl$_3$): δ=0.99 (s, 9H); 1.02 (s, 6 H); 1.63 (s, 2 H); 3.37 (br. s, 2 H); 7.50 (t, 1 H, J=6.8 Hz); 7.79 (dd, 1 H, J=4.9 Hz, J=2.6 Hz); 7.85 (d), 1 H, J=3.8 Hz); 7.88-7.95 (m, 2 H); 8.36 (d), 1 H, J=1.5 Hz); 8.85 (d), 1 H, J=6.8 Hz).

Example 3

(7-Methyl-2-thiophen-3-yl-imidazo[1,2-a]pyridin-3-yl)-(1,1,3,3-tetramethylbutyl)-amine hydrochloride As described for Example 1, 11.7 g of crude product were obtained from 3.57 g (33.0 mmol) of 4-methylpyridin-2-ylamine, 4.83 g (43.1 mmol) of thiophene-3-carbaldehyde, 4.00 g (28.7 mmol) of 2-isocyano-2,4,4-trimethylpentane (1,1,3,3-tetramethylbutylisonitrile) and 2.8 ml of aqueous perchloric acid (20 wt. % strength) in 60 ml dichloromethane. The crude product was heated to reflux in 150 ml of hexane, after cooling with stirring, the suspended solid was filtered out and dried under reduced pressure, 5.75 g of solid being obtained. 1.5 g of this solid were dissolved in 12 ml of 2-butanone and combined with ice cooling with 43 µl of water and 0.61 ml of chlorotrimethylsilane. After stirring overnight, the resultant hydrochloride of (7-methyl-2-thiophen-3-yl-imidazo[1,2-a]pyridin-3-yl)-(1,1,3,3-tetramethylbutyl)amine was filtered out and dried (yield 1.54 g).

$^1$H-NMR (600 MHz, CDCl$_3$): δ=0.98 (s, 9H); 1.01 (s, 6 H); 1.62 (s, 2 H); 2.56 (s, 3 H); 3.34 (br. s, 2 H); 7.35 (t, 1 H, J=6.8 Hz); 7.66 (s, 1 H); 7.77 (dd, 1 H, J=4.9 Hz, J=2.6 Hz); 7.82 (d), 1 H, J=6.0 Hz); 8.31 (s, 1 H); 8.72 (d), 1 H, J=6.8 Hz).

Example 4

(2-Furan-3-yl-imidazo[1,2-a]pyridin-3-yl)-(1,1,3,3-tetramethylbutyl)amine hydrochloride As described for Example 1, 8.61 g of crude product were obtained from 3.13 g (28.9 mmol) of 4-methylpyridin-2-ylamine, 3.62 g (37.7 mmol) of furan-3-carbaldehyde, 3.50 g (25.1 mmol) of 2-isocyano-2,4,4-trimethylpentane (1,1,3,3- tetramethylbutylisonitrile) and 2.5 ml of aqueous perchloric acid (20 wt. % strength) in 50 ml of dichloromethane. The crude product was heated to reflux in 250 ml of hexane, after cooling with stirring, the suspended solid was filtered out and dried under reduced pressure, 2.89 g of solid being obtained. 1.5 g of this solid were dissolved in 12 ml of 2-butanone and combined with ice cooling with 46 µl of water and 0.64 ml of chlorotrimethylsilane. After stirring overnight, the resultant hydrochloride was filtered off from (2-furan-3-yl-imidazo[1,2-a]pyridin-3-yl)-(1,1,3,3-tetramethylbutyl)amine and dried (yield: 1.64 g).

$^1$H-NMR (600 MHz, CDCl$_3$): δ=1.02 (s, 9H); 1.08 (s, 6 H); 1.69 (s, 2 H); 3.36 (br. s, 2 H); 7.23 (s, 1 H); 7.48 (t, 1 H, J=6.4 Hz); 7.85-7.94 (m, 2 H); 8.51 (s, 1 H).

Example 5

(2-Furan-3-yl-7-methyl-imidazo[1,2-a]pyridin-3-yl)-(1,1,3,3-tetramethylbutyl)amine hydrochloride As described for Example 1, 7.13 g of crude product were obtained from 2.72 g (28.9 mmol) of 2-aminopyridine, 3.62 g (37.7 mmol) of furan-3-carbaldehyde, 3.50 g (25.1 mmol) of 2-isocyano-2,4,4-tri-methylpentane (1,1,3,3-tetramethylbutylisonitrile) and 2.5 ml of aqueous perchloric acid (20 wt. % strength) in 50 ml of dichloromethane.

$^1$H-NMR (600 MHz, CDCl$_3$): δ=1.01 (s, 9 H); 1.07 (s, 6 H); 1.67 (s, 2 H); 2.56 (s, 3 H); 3.34 (br. s, 2 H); 7.20 (s, 1 H); 7.33 (d), 1 H, J=6.8 Hz); 7.66 (s, 1 H); 7.85 (s, 1 H); 8.48 (s, 1 H); 8.96 (d, 1 H, J=6.8 Hz).

The compounds of Examples 6 through 35 were produced in a manner similar to Example 1. The starting compounds corresponding to formulas II, III and IV used in each case shown in the following Table I:

TABLE I

| Example | Compound corresponding to formula II | Compound corresponding to formula III | Compound corresponding to formula IV |
|---|---|---|---|
| 6 | 2-amino-pyridine | furan-3-carbaldehyde | heptylisonitrile |
| 7 | 2-amino-pyridine | furan-3-carbaldehyde | 1,1-dimethyl-hexylisonitrile |
| 8 | 2-amino-pyridine | furan-3-carbaldehyde | 1,1-dimethyloctyl-isonitrile |
| 9 | 2-amino-pyridine | thiophene-3-carbaldehyde | heptylisonitrile |
| 10 | 2-amino-pyridine | thiophene-3-carbaldehyde | 1,1-dimethyl-hexylisonitirile |
| 11 | 4-methyl-pyridin-2-yl-amine | furan-3-carbaldehyde | heptylisonitrile |
| 12 | 4-methyl-pyridin-2-yl-amine | furan-3-carbaldehyde | octylisonitrile |
| 13 | 4-methyl-pyridin-2-yl-amine | furan-3-carbaldehyde | nonylisonitrile |
| 14 | 4-methyl-pyridin-2-yl-amine | furan-3-carbaldehyde | 1,1-dimethyl-hexyl-isonitrile |
| 15 | 4-methyl-pyridin-2-yl-amine | furan-3-carbaldehyde | 1,1-dimethyl-heptyl-isonitrile |
| 16 | 4-methyl-pyridin-2-yl-amine | furan-3-carbaldehyde | 1,1-dimethyl-octyl-isonitrile |
| 17 | 4-methyl-pyridin-2-yl-amine | thiophene-3-carbaldehyde | 1,1-dimethylhexyl-isonitrile |
| 18 | 4-methyl-pyridin-2-yl-amine | thiophene-3-carbaldehyde | 1,1-dimethylheptyl-isonitrile |
| 19 | 4-methyl-pyridin-2-yl-amine | thiophene-3-carbaldehyde | 1,1-dimethyloctyl-isonitrile |
| 20 | 4-methyl-pyridin-2-yl-amine | pyridine-2-carbaldehyde | octylisonitrile |
| 21 | 4-methyl-pyridin-2-yl-amine | pyridine-2-carbaldehyde | 1,1-dimethylhexyl-isonitrile |
| 22 | 4-methyl-pyridin-2-yl-amine | pyridine-2-carbaldehyde | 1,1-dimethyloctyl-isonitrile |
| 23 | 4-methyl-pyridin-2-yl-amine | pyridine-3-carbaldehyde | nonylisonitrile |
| 24 | 4-methyl-pyridin-2-yl-amine | pyridine-3-carbaldehyde | heptylisonitrile |
| 25 | 4-methyl-pyridin-2-yl-amine | pyridine-4-carbaldehyde | octylisonitrile |
| 26 | 4-methyl-pyridin-2-yl-amine | pyridine-4-carbaldehyde | 1,1-dimethylhexyl-isonitrile |
| 27 | 5-methyl-pyridin-2-yl-amine | furan-3-carbaldehyde | octylisonitrile |
| 28 | 5-methyl-pyridin-2-yl-amine | furan-3-carbaldehyde | 1,1-dimethylhexyl-isonitrile |
| 29 | 5-methyl-pyridin-2-yl-amine | pyridine-2-carbaldehyde | hexadecylisonitrile |
| 30 | 5-methyl-pyridin-2-yl-amine | pyridine-2-carbaldehyde | 1,1-dimethylheptyl-isonitrile |
| 31 | 6-methyl-pyridin-2-yl-amine | pyridine-2-carbaldehyde | 1,1-dimethylheptyl-isonitrile |
| 32 | 2-amino-3,5-dichloropyridine | thiophene-3-carbaldehyde | hexadecylisonitrile |
| 33 | 4-methyl-pyridin-2-yl-amine | thiophene-3-carbaldehyde | benzylisonitrile |
| 34 | 4-methyl-pyridin-2-yl-amine | phenyl-carbaldehyde | 1,1-dimethylhexyl-isonitrile |
| 35 | 4-methyl-pyridin-2-yl-amine | furan-3-carbaldehyde | 1,1-dimethylheptyl-isonitrile |

Example 6

(2-Furan-3-yl-imidazo[1,2-a]pyridin-3-yl)-heptyl-amine hydrochloride $^1$H-NMR (600 MHz, CDCl$_3$): δ=0.86 (t, 3 H, J=7.6 Hz); 1.24 (m, 6 H); 1.34 (m, 2 H); 1.59 (m, 2 H); 2.98 (t, 2 H, J=7.6 Hz); 7.06 (s, 1 H); 7.17 (dd, 1 H, J$_1$=J$_2$=6.8 Hz); 7.23 (s, 1 H); 7.27 (s, 1 H); 7.51 (dd, 1 H, J$_1$=J$_2$=7.9 Hz); 7.82 (d), 1 H, J=8.3 Hz); 8.23 (s, 1 H); 8.42 (d, 1 H, J=8.3 Hz); 15.18 (s, 1 H).

Example 7

(1,1-Dimethyl-hexyl)-(2-furan-3-yl-imidazo[1,2-a]pyridin-3-yl)-amine hydrochloride

MS (APCI) =312 [M$^+$]

Example 8

(1,1-Dimethyl-octyl)-(2-furan-3-yl-imidazo[1,2-a]pyridin-3-yl)-amine hydrochloride $^1$H-NMR (600 MHz, CDCl$_3$): δ=0.88 (t, 3 H, J=6.8 Hz); 1.03 (s, 6 H); 1.21-1.32 (m, 8 H); 1.35-1.42 (m, 2 H); 1.49-1.57 (m, 2 H); 7.11 (s, 1 H); 7.16 (t, 1 H, J=6.8 Hz); 7.28-7.31 (m, 2 H); 7.53 (t, 1 H, J=7.5 Hz); 7.90 (d), 1 H, J=8.3 Hz); 8.33-8.37 (m, 1 H); 8.53 (d, 1 H, J=6.8 Hz); 15.40 (s, 1 H).

Example 9

Heptyl-(2-thiophen-3-yl-imidazo[1,2-a]pyridin-3-yl)-amine hydrochloride $^1$H-NMR (600 MHz, CDCl$_3$): δ=0.86 (t, 3 H, J=6.8 Hz); 1.19-1.30 (m, 6 H); 1.56-1.64 (m, 2 H); 2.95-3.15 (m, 2 H);

7.11 (d), 1 H, J=6.8 Hz); 7.24-7.26 (m, 1 H); 7.44-7.47 (m, 1 H); 7.76 (d), 1 H, J=5.3 Hz); 7.85 (d), 1 H, J=9.1 Hz); 8.20-8.23 (m, 1 H); 8.41 (d), 1 H, J=6.8 Hz); 15.07 (s, 1 H).

Example 10

(1,1-Dimethyl-hexyl)-(2-thiophen-3-yl-imidazo[1,2-a]pyridin-3-yl)-amine hydrochloride $^1$H-NMR (600 MHz, CDCl$_3$): δ=0.87 (t, 3 H, J=6.8 Hz); 0.97 (s, 6 H); 1.21 (m, 4 H); 1.28 (m, 2 H); 1.34 (m, 2 H); 1.48 (m, 2 H); 7.12 (dd, 1 H, J$_1$=J$_2$=6.8 Hz); 7.25 (s, 1 H); 7.47 (dd, 1 H, J$_1$=9.1 Hz, J$_2$=6.8 Hz); 7.78 (d), 1 H, J=4.5 Hz); 7.88 (d), 1 H, J=9.1 Hz); 8.28 (s, 1 H); 8.56 (d), 1 H, J=6.8 Hz); 15.17 (s, 1 H).

Example 11

(2-Furan-3-yl-7-methyl-imidazo[1,2-a]pyridin-3-yl)-heptyl-amine hydrochloride $^1$H-NMR (600 MHz, CDCl$_3$): δ=0.86 (t, 3 H, J=6.8 Hz); 1.19-1.35 (m, 8 H); 1.54-1.62 (m, 2 H); 2.45 (s, 3 H); 2.95-3.00 (m, 2 H); 6.97 (d), 1 H, J=6.8 Hz); 7.05 (s, 1 H); 7.29 (s, 1 H); 7.61 (s, 1 H); 8.21 (s, 1 H); 8.29 (d), 1 H, J=6.8 Hz); 14.83 (s, 1 H).

Example 12

(2-Furan-3-yl-7-methyl-imidazo[1,2-a]pyridin-3-yl)-octyl-amine hydrochloride $^1$H-NMR (600 MHz, CDCl$_3$): δ=0.86 (t, 3 H, J=6.8 Hz); 1.19-1.35 (m, 10 H); 1.54-1.60 (m, 2 H); 2.45 (s, 3 H); 2.97 (t, 2 H, J=7.5 Hz); 6.98 (d), 1 H, J=6.8 Hz); 7.02 (s, 1 H); 7.29 (s, 1 H); 7.59 (s, 1 H); 8.17 (s, 1 H); 8.27 (d), 1 H, J=6.8 Hz); 14.45 (s, 1 H).

Example 13

(2-Furan-3-yl-7-methyl-imidazo[1,2-a]pyridin-3-yl)-nonyl-amine hydrochloride $^1$H-NMR (600 MHz, CDCl$_3$): δ=0.87 (t, 3 H, J=6.8 Hz); 1.19-1.31 (m, 8 H); 1.53-1.64 (m, 6 H); 2.46 (s, 3 H); 2.99 (t, 2 H, J=7.6 Hz); 6.97 (d), 1 H, J=6.8 Hz); 7.08 (s, 1 H); 7.32 (s, 1 H); 7.69 (s, 1 H); 8.23 (d), 1 H, J=6.8 Hz); 8.26 (s, 1 H); 15.29 (s, 1 H).

Example 14

(1,1-Dimethyl-hexyl)-(2-furan-3-yl-7-methyl-imidazo[1,2-a]pyridin-3-yl)-amine hydrochloride $^1$H-NMR (600 MHz, CDCl$_3$): δ=0.90 (t, 3 H, J=7.2 Hz); 1.03 (s, 6 H); 1.26 (m, 4 H); 1.38 (m, 2 H); 1.51 (m, 2 H); 2.48 (s, 3 H); 6.96 (d), 1 H, J=6.8 Hz); 7.10 (s, 1 H); 7.27 (s, 1 H); 7.31 (s, 1 H); 7.71 (s, 1 H); 8.34 (m, 2 H); 15.28 (s, 1 H).

Example 15

(1,1-Dimethyl-heptyl)-(2-furan-3-yl-7-methyl-imidazo[1,2-a]pyridin-3-yl)-amine hydrochloride

MS (APCI)=340 [M$^+$]

Example 16

(1,1-Dimethyl-octyl)-(2-furan-3-yl-7-methyl-imidazo[1,2-a]pyridin-3-yl)-amine hydrochloride

MS (APCI)=354 [M$^+$]

Example 17

(1,1-Dimethyl-hexyl)-(7-methyl-2-thiophen-3-yl-imidazo[1,2-a]pyridin-3-yl)-amine hydrochloride

MS (APCI)=342 [M$^+$]

Example 18

(1,1-Dimethyl-heptyl)-(7-methyl-2-thiophen-3-yl-imidazo[1,2-a]pyridin-3-yl)-amine hydrochloride

MS (APCI)=356 [M$^+$]

Example 19

(1,1-Dimethyl-octyl)-(7-methyl-2-thiophen-3-yl-imidazo[1,2-a]pyridin-3-yl)-amine

MS (APCI)=370 [M$^+$]

Example 20

(7-Methyl-2-pyridin-2-yl-imidazo[1,2-a]pyridin-3-yl)-octyl-amine hydrochloride

MS (APCI)=337 [M$^+$]

Example 21

(1,1-Dimethyl-hexyl)-(7-methyl-2-pyridin-2-yl-imidazo[1,2-a]pyridin-3-yl)-amine hydrochloride

MS (APCI)=337 [M$^+$]

Example 22

(1,1-Dimethyl-octyl)-(7-methyl-2-pyridin-2-yl-imidazo[1,2-a]pyridin-3-yi)-amine hydrochloride

MS (APCI)=365 [M$^+$]

Example 23

(7-Methyl-2-pyridin-3-yl-imidazo[1,2-a]pyridin-3-yl)-nonyl-amine hydrochloride

MS (ESI)=351 [M$^+$]

Example 24

Heptyl-(7-methyl-2-pyridine-4-yl-imidazo[1,2-a]pyridin-3-yl)-amine hydrochloride

MS (APCI)=323 [M$^+$]

Example 25

(7-Methyl-2-pyridin-4-yl-imidazo[1,2-a]pyridin-3-yl)-octyl-amine hydrochloride

MS (APCI)=337 [M$^+$]

Example 26

(1,1-Dimethyl-hexyl)-(7-methyl-2-pyridin-4-yl-imidazo[1,2-a]pyridin-3-yl)-amine hydrochloride

MS (APCI)=337 [M+]

Example 27

(2-Furan-3-yl-6-methyl-imidazo[1,2-a]pyridin-3-yl)-octyl-amine hydrochloride $^1$H-NMR (600 MHz, CDCl$_3$): δ=0.87 (t, 3 H, J=6.8 Hz); 1.26 (m, 8 H); 1.36 (m, 2 H); 1.59 (m, 2 H); 2.43 (s, 3 H); 2.97 (t, 2 H, J=7.6 Hz); 7.04 (s, 1 H); 7.30 (s, 1 H); 7.33 (d), 1 H, J=9.1 Hz); 7.73 (d), 1 H, J=9.1 Hz); 8.16 (s, 1 H); 8.18 (s, 1 H); 14.79 (s, 1 H).

Example 28

(1,1-Dimethyl-hexyl)-(2-furan-3-yl-6-methyl-imidazo[1,2-a]pyridin-3-yl)-amine hydrochloride

MS (APCI)=326 [M+]

Example 29

Hexadecyl-(6-methyl-2-pyridin-2-yl-imidazo[1,2-a]pyridin-3-yl)-amine hydrochloride $^1$H-NMR (600 MHz, CDCl$_3$): δ=0.88 (t, 3 H, J=6.8 Hz); 1.15-1.34 (m, 26 H); 1.53-1.58 (m, 2 H); 2.55 (s, 3 H); 3.11 (d), 1 H, J=6.8Hz); 3.12(d), 1 H, J=7.5Hz); 7.71 (d), 1 H, J=9.1 Hz); 7.76 (t, 1 H, J=6.5 Hz); 8.15 (d), 1 H, J=9.1 Hz); 8.29 (s, 1 H); 8.43 (t, 1 H, J=8.0 Hz); 8.81 (d), 1 H, J=5.3 Hz), 8.93 (d), 1 H, J=8.0 Hz), 14.40 (s, 1 H).

Example 30

(1,1-Dimethyl-heptyl)-(6-methyl-2-pyridin-2-yl-imidazo[1,2-a]pyridin-3-yl)-amine hydrochloride $^1$H-NMR (600 MHz, CDCl$_3$): δ=0.88 (t, 3 H, J=6.8 Hz); 0.94 (s, 6 H); 1.15-1.39 (m, 8 H); 2.54 (s, 3 H); 7.76 (d), 1 H, J=9.1 Hz); 7.93-7.99 (m, 1 H,; 8.13 (d), 1 H, J=9.1 Hz); 8.49 (s, 1 H); 8.60 (t, 1 H, J=7.6 Hz); 8.88 (d), 1 H, J=5.3 Hz), 8.94 (d), 1 H, J=7.6 Hz), 14.40 (s, 1 H).

Example 31

(1,1-Dimethyl-heptyl)-(5-methyl-2-pyridin-2-yl-imidazo[1,2-a]pyridin-3-yl)-amine hydrochloride

MS (APCI)=351 [M+], 225, 198

Example 32

(6,8-Dichloro-2-thiophen-3-yl-imidazo[1,2-a]pyridin-3-yl)-hexadecyl-amine hydrochloride

MS (APCI)=508 [M+]

Example 33

Benzyl-(7-methyl-2-thiophen-3-yl-imidazo[1,2-a]pyridin-3-yl)-amine

Example 34

(1,1-Dimethyl-hexyl)-(7-methyl-2-phenyl-imidazo[1,2-a]pyridin-3-yl)-amine

Example 35

(1,1-Dimethyl-hexyl)-(2-furan-3-yl-7-methyl-imidazo[1,2-a]pyridin-3-yl)-amine

Pharmacological data:

Reference data for a few selected comparison substances known to persons skilled in the art for the method for determining VR-1 receptor affinity are shown in the following Table A:

TABLE A

| Substance | IC50 (μM) |
| --- | --- |
| Resiniferatoxin | 0.00021 |
| Capsaicin | 3.20 |
| Dihydrocapsaicin | 2.72 |
| Isovelleral | 7.22 |
| Arvanil | 8.90 |

The pharmacological data for the substituted imidazo[1,2-a]pyridine compounds according to the invention or the substituted imidazo[1,2-a]pyridine compounds used according to the invention were determined as described above and are shown in the following Tables B and C:

TABLE B

| Compound according to Example | % Activation [1] | % Inhibition [1] | EC$_{50}$ [1] | % VR1 binding % inhibition at 10 μM [2] | CB1 binding % inhibition at 10 μM [3] |
| --- | --- | --- | --- | --- | --- |
| 2 | | 32.2 | 5.4 | 36 | 47 |
| 3 | 30.1 | 65 | 0.8 | | 35.5 |
| 4 | | 44.1 | | | 35 |
| 5 | 32.4 | 80.7 | 5.9 | | 32.7 |
| 1 | | | 9.4 | 42.5 | 43 |

[1] according to method (b), in each case means from 4–5 measurements
[2] according to method (a)
[3] according to method (c)

TABLE C

| * | R¹ | R² | R³ | R⁴ | R⁵ | R⁶ | VR1[4] | VR1[5] |
|---|----|----|----|----|----|----|--------|--------|
| 6 | H | H | H | H | 3-furyl | (CH₂)₆CH₃ | 66.4 | |
| 7 | H | H | H | H | 3-furyl | C(CH₃)₂(CH₂)₄CH₃ | 46 | |
| 11 | H | Me | H | H | 3-furyl | (CH₂)₆CH₃ | 81.7 | 50.3 |
| 12 | H | Me | H | H | 3-furyl | (CH₂)₇CH₃ | 84.6 | 36.9 |
| 14 | H | Me | H | H | 3-furyl | C(CH₃)₂(CH₂)₄CH₃ | 97.9 | 52.1 |
| 15 | H | Me | H | H | 3-furyl | C(CH₃)₂(CH₂)₅CH₃ | 92.5 | 49 |
| 16 | H | Me | H | H | 3-furyl | C(CH₃)₂(CH₂)₆CH₃ | 31.8 | |
| 17 | H | Me | H | H | 3-thiophene | C(CH₃)₂(CH₂)₄CH₃ | 97.5 | 68.9 |
| 18 | H | Me | H | H | 3-thiophene | C(CH₃)₂(CH₂)₅CH₃ | 62.8 | 45.3 |
| 23 | H | Me | H | H | 3-pyridine | (CH₂)₈CH₃ | 34.4 | |
| 25 | H | Me | H | H | 4-pyridine | (CH₂)₇CH₃ | 33.2 | |
| 26 | H | Me | H | H | 4-pyridine | C(CH₃)₂(CH₂)₄CH₃ | 32.1 | |
| 27 | H | H | Me | H | 3-furyl | (CH₂)₇CH₃ | 61.1 | |
| 28 | H | H | Me | H | 3-furyl | C(CH₃)₂(CH₂)₄CH₃ | 36.6 | |

* Compound according to Example
[4]VR1 inhibition in rats (10 μM) [%], according to method (b), in each case 1–3 measurements
[5]VR1 activation in rats (10 μM) [%], according to method (b), in each case 1–3 measurements The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A substituted imidazo[1,2-a]pyridine compound corresponding to formula (I):

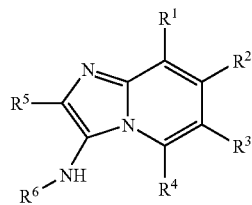

wherein:

R¹, R², R³ and R⁴ may be identical or different and respectively denote hydrogen, halogen, a hydroxy group, a cyano group, a nitro group, an amino group, a carboxy group, a —C(=O)—R⁷ group, a —(C=O)—OR⁸ group, an OR⁹ group, a linear or branched, saturated or unsaturated, optionally at least monosubstituted aliphatic residue, a saturated or unsaturated, optionally at least monosubstituted cycloaliphatic residue optionally attached via an alkylene group, or two adjacent residues R¹ and R², R² and R³ or R³ and R⁴, respectively, together form a 3- or 4-membered, saturated or unsaturated, aliphatic ring optionally comprising at least one heteroatom as a ring member, and the remaining residues R³ and R⁴, R¹ and R⁴ or R¹ and R², respectively, each denote hydrogen;

R⁵ denotes a linear or branched, saturated or unsaturated, optionally at least monosubstituted aliphatic residue, a saturated or unsaturated, optionally at least monosubstituted cycloaliphatic residue optionally comprising at least one heteroatom as a ring member, wherein said cycloaliphatic residue optionally is attached via an alkylene group and optionally may be fused with an optionally at least monosubstituted, mono- or polycyclic ring system, an optionally at least monosubstituted phenyl residue optionally attached via an alkylene group, wherein said phenyl residue optionally may be fused with an optionally at least monosubstituted, mono- or polycyclic ring system; and wherein the optional substituents on the phenyl residue or the mono- or polycyclic ring system are selected from the group consisting of $C_{1-4}$ alkoxy, $C_{1-4}$ alkyl, hydroxy, halogen, —CHF₂, —CH₂F, —CF₃, phenyl, phenoxy, cyano, nitro, amino and di-($C_{1-3}$)-alkylamino; or an optionally at least monosubstituted heteroaryl residue optionally attached via an alkylene group, which heteroaryl residue may be fused with an optionally at least monosubstituted, mono- or polycyclic ring system;

R⁶ denotes a linear or branched, saturated or unsaturated, optionally at least monosubstituted aliphatic residue with more than 12 carbon atoms;

R⁷ denotes a linear or branched, saturated or unsaturated, optionally at least monosubstituted aliphatic residue, a saturated or unsaturated, optionally at least monosubstituted cycloaliphatic residue optionally comprising at least one heteroatom as a ring member, wherein said cycloaliphatic residue optionally may be attached via an alkylene group and optionally may be fused with an optionally at least monosubstituted, mono- or polycyclic ring system, or an optionally at least monosubstituted aryl or heteroaryl residue optionally attached via an alkylene group, wherein said aryl or heteroaryl residue optionally may be fused with an optionally at least monosubstituted, mono- or polycyclic ring system;

R⁸ denotes a linear or branched, saturated or unsaturated, optionally at least monosubstituted aliphatic residue, a saturated or unsaturated, optionally at least monosubstituted cycloaliphatic residue optionally comprising at least one heteroatom as a ring member, wherein said cycloaliphatic residue optionally is attached via an alkylene group and optionally may be fused with an optionally at least monosubstituted, mono- or polycyclic ring system, or an optionally at least monosubstituted aryl or heteroaryl residue optionally attached via an alkylene group, wherein said aryl or heteroaryl residue optionally may be fused with an optionally at least monosubstituted, mono- or polycyclic ring system;

R⁹ denotes a linear or branched, saturated or unsaturated, optionally at least monosubstituted aliphatic residue, a saturated or unsaturated, optionally at least monosubstituted cycloaliphatic residue optionally comprising at least one heteroatom as a ring member, wherein said cycloaliphatic residue optionally is attached via an alkylene group and optionally may be fused with an optionally at least monosubstituted, mono- or polycyclic ring system, or an optionally at least monosubstituted aryl or heteroaryl residue optionally attached via an alkylene group, wherein said aryl or heteroaryl residue optionally may be fused with an optionally at least monosubstituted, mono- or polycyclic ring system;

in the form of a pure stereoisomer or a mixture of stereoisomers in any mixing ratio, or a corresponding salt thereof.

2. A compound according to claim 1, wherein said compound is in the form of a pure enantiomer or diastereomer.

3. A compound according to claim 1, wherein said compound is in the form of a racemic mixture.

4. A compound according to claim 1, wherein $R^1$, $R^2$, $R^3$ and $R^4$, may be identical or different and respectively denote hydrogen, halogen, a hydroxy group, a cyano group, a nitro group, an amino group, a carboxy group, a —C(=O)—$R^7$ group, a —(C=O)—$OR^8$ group, an $OR^9$ group, a linear or branched, saturated or unsaturated, optionally at least monosubstituted aliphatic $C_{1-12}$ residue, a saturated or unsaturated, optionally at least monosubstituted cycloaliphatic $C_{3-8}$ residue optionally attached via a $C_{1-8}$ alkylene group, or two adjacent residues $R^1$ and $R^2$, $R^2$ and $R^3$ or $R^3$ and $R^4$, respectively, together form a 3- or 4-membered, saturated or unsaturated, aliphatic ring optionally comprising at least one heteroatom as a ring member, and the remaining residues $R^3$ and $R^4$, $R^1$ and $R^4$ or $R^1$ and $R^2$, respectively denote hydrogen.

5. A compound according to claim 4, wherein $R^1$, $R^2$, $R^3$ and $R^4$ may be identical or different and each respectively denote hydrogen, F, Cl, Br, a hydroxy group, a carboxy group, a —C(=O)—$R^7$ group, a —(C=O)—$OR^8$ group, an $OR^9$ group or a linear or branched $C_{1-12}$ alkyl residue.

6. A compound according to claim 5, wherein $R^1$, $R^2$, $R^3$ and $R^4$ may be identical or different and each respectively denote hydrogen, F, Cl or a linear or branched $C_{1-4}$ alkyl residue.

7. A compound according to claim 1, wherein $R^5$ denotes a linear or branched, saturated or unsaturated, optionally at least monosubstituted aliphatic $C_{1-12}$ residue, a saturated or unsaturated, optionally at least monosubstituted cycloaliphatic $C_{3-8}$ residue optionally comprising at least one heteroatom as a ring member, wherein said cycloaliphatic residue optionally is attached via a $C_{1-8}$ alkylene group and optionally may be fused with an optionally at least monosubstituted, mono- or polycyclic ring system, an optionally at least monosubstituted phenyl residue optionally attached via a $C_{1-8}$ alkylene group, wherein said phenyl residue optionally may be fused with an optionally at least monosubstituted, mono- or polycyclic ring system; wherein the optional substituents on the phenyl residue and the mono- or polycyclic ring system are selected from the group consisting of $C_{1-4}$ alkoxy, $C_{1-4}$ alkyl, hydroxy, halogen, —$CHF_2$, —$CH_2F$, —$CF_3$, phenyl, phenoxy, cyano, nitro, amino and di-($C_{1-3}$)-alkylamino, or an optionally at least monosubstituted 5- or 6-membered heteroaryl residue optionally attached via a $C_{1-8}$ alkylene group, wherein said heteroaryl residue optionally may be fused with an optionally at least monosubstituted, mono- or polycyclic ring system.

8. A compound according to claim 7, wherein $R^5$ denotes a linear or branched $C_{1-8}$ alkyl residue; a saturated or unsaturated, optionally at least monosubstituted cycloaliphatic $C_{3-8}$ residue optionally comprising at least one heteroatom as a ring member, wherein said cycloaliphatic residue optionally may be attached via a $C_{1-3}$ alkylene group; an optionally at least monosubstituted phenyl residue optionally attached via a $C_{1-3}$ alkylene group, wherein the optional substituents on the phenyl residue independently of each other are selected from the group consisting of $C_{1-4}$ alkoxy, $C_{1-4}$ alkyl, hydroxy, halogen, —$CHF_2$, —$CH_2F$, —$CF_3$, phenyl, phenoxy, cyano, nitro, amino and di-($C_{1-3}$)-alkylamino, or an at least monosubstituted, 5- or 6-membered heteroaryl residue optionally attached via a $C_{1-3}$ alkylene group.

9. A compound according to claim 8, wherein $R^5$ denotes a residue selected from the group consisting of optionally at least monosubstituted phenyl, wherein the optional substituents on the phenyl residue are independently selected from the group consisting of $C_{1-4}$ alkoxy, $C_{1-4}$ alkyl, hydroxy, halogen, —$CHF_2$, —$CH_2F$, —$CF_3$, phenyl, phenoxy, cyano, nitro, amino and di-($C_{1-3}$)-alkylamino; optionally at least monosubstituted furyl; optionally at least monosubstituted thienyl, and optionally at least monosubstituted pyridyl.

10. A compound according to claim 9, wherein $R^5$ denotes a residue selected from the group consisting of 2-furyl, 3-furyl, 2-thienyl, 3-thienyl, 2-pyridyl, 3-pyridyl, 4-pyridyl and phenyl.

11. A compound according to claim 1, wherein $R^6$ denotes a linear or branched, saturated or unsaturated, optionally at least monosubstituted aliphatic residue with 13-30 carbon atoms.

12. A compound according to claim 11, wherein $R^6$ denotes a linear or branched, saturated or unsaturated, optionally at least monosubstituted aliphatic residue with 13-20 carbon atoms.

13. A compound according to claim 1, wherein $R^7$ denotes a linear or branched, saturated or unsaturated, optionally at least monosubstituted aliphatic $C_{1-8}$ residue, a saturated or unsaturated, optionally at least monosubstituted cycloaliphatic $C_{3-8}$ residue optionally comprising at least one heteroatom as a ring member, wherein said cycloaliphatic residue optionally may be attached via a $C_{1-8}$ alkylene group and optionally may be fused with an optionally at least monosubstituted, mono- or polycyclic ring system, or an optionally at least monosubstituted, 5- or 6-membered aryl or heteroaryl residue optionally attached via a $C_{1-8}$ alkylene group, wherein said aryl or heteroaryl residue optionally may be fused with an optionally at least monosubstituted, mono- or polycyclic ring system.

14. A compound according to claim 13, wherein $R^7$ denotes a linear or branched $C_{1-4}$ alkyl residue, a saturated or unsaturated, optionally at least monosubstituted cycloaliphatic $C_{3-8}$ residue optionally comprising at least one heteroatom as a ring member, wherein said cycloaliphatic residue optionally may be attached via a $C_{1-3}$ alkylene group, or an optionally at least monosubstituted, 5- or 6-membered aryl or heteroaryl residue optionally attached via a $C_{1-3}$ alkylene group, wherein said aryl or heteroaryl residue optionally may be fused with an optionally at least monosubstituted, mono- or polycyclic ring system.

15. A compound according to claim 1, wherein $R^8$ denotes a linear or branched, saturated or unsaturated, optionally at least monosubstituted aliphatic $C_{1-8}$ residue; a saturated or unsaturated, optionally at least monosubstituted cycloaliphatic $C_{3-8}$ residue optionally comprising at least one heteroatom as a ring member, wherein said cycloaliphatic residue optionally may be attached via a $C_{1-8}$ alkylene group and optionally may be fused with an optionally at least monosubstituted, mono- or polycyclic ring system; or an optionally at least monosubstituted, 5- or 6-membered aryl or heteroaryl residue optionally attached via a $C_{1-8}$ alkylene group, wherein said aryl or heteroaryl residue optionally may be fused with an optionally at least monosubstituted, mono- or polycyclic ring system.

16. A compound according to claim 15, wherein $R^8$ denotes a linear or branched $C_{1-4}$ alkyl residue; a saturated or unsaturated, optionally at least monosubstituted cycloaliphatic $C_{3-8}$ residue optionally comprising at least one heteroatom as a ring member, wherein said cycloaliphatic residue optionally may be attached via a $C_{1-3}$ alkylene group; or an optionally at least monosubstituted, 5- or 6-membered aryl or heteroaryl residue optionally attached via a $C_{1-3}$ alkylene group, wherein said aryl or heteroaryl residue optionally may be fused with an optionally at least monosubstituted, mono- or polycyclic ring system.

17. A compound according to claim 1, wherein $R^9$ denotes a linear or branched, saturated or unsaturated, optionally at least monosubstituted aliphatic $C_{1-8}$ residue; a saturated or unsaturated, optionally at least monosubstituted cycloaliphatic $C_{3-8}$ residue optionally comprising at least one heteroatom as a ring member, wherein said cycloaliphatic residue optionally may be attached via a $C_{1-8}$ alkylene group and optionally may be fused with an optionally at least monosubstituted, mono- or polycyclic ring system; or an optionally at least monosubstituted, 5- or 6-membered aryl or heteroaryl residue optionally attached via a $C_{1-8}$ alkylene group, wherein said aryl or heteroaryl residue optionally may be fused with an optionally at least monosubstituted, mono- or polycyclic ring system.

18. A compound according to claim 17, wherein $R^9$ denotes a linear or branched $C_{1-4}$ alkyl residue; a saturated or unsaturated, optionally at least monosubstituted cycloaliphatic $C_{3-8}$ residue optionally comprising at least one heteroatom as a ring member, wherein said cycloaliphatic residue optionally may be attached via a $C_{1-3}$ alkylene group; or an optionally at least monosubstituted, 5- or 6-membered aryl or heteroaryl residue optionally attached via a $C_{1-3}$ alkylene group, wherein said aryl or heteroaryl residue optionally may be fused with an optionally at least monosubstituted, mono- or polycyclic ring system.

19. A compound according to claim 1, wherein:
$R^1$, $R^2$, $R^3$ and $R^4$, respectively, independently denote hydrogen, halogen, a hydroxy group, a cyano group, a nitro group, an amino group, a carboxy group, a —C(=O)—$R^7$ group, a —C(=O)—$OR^8$ group, an —$OR^9$ group, a linear or branched, saturated or unsaturated, optionally substituted $C_{1-12}$ aliphatic residue; an unsaturated or saturated, optionally substituted 3-, 4-, 5-, 6-, 7- or 8-membered cycloaliphatic residue, which may be attached via a linear or branched $C_{1-8}$ alkylene group; or two adjacent residues $R^1$ and $R^2$, $R^2$ and $R^3$ or $R^3$ and $R^4$, respectively, together form a 3- or 4-membered, saturated or unsaturated, aliphatic ring optionally comprising 1 or 2 heteroatoms selected from the group consisting of oxygen, nitrogen and sulfur as ring members, and the remaining residues $R^3$ and $R^4$, $R^1$ and $R^4$ or $R^1$ and $R^2$, respectively, each denote hydrogen;

$R^5$ denotes a linear or branched, saturated or unsaturated, optionally substituted $C_{1-12}$ aliphatic residue; an unsaturated or saturated, optionally substituted 3-, 4-, 5-, 6-, 7- or 8-membered cycloaliphatic residue, which may comprise 1, 2 or 3 heteroatom(s) independently selected from the group consisting of oxygen, nitrogen and sulfur as ring member(s), wherein said cycloaliphatic residue optionally may be attached via a linear or branched $C_{1-8}$ alkylene group and optionally may be fused with a saturated or unsaturated, optionally substituted mono- or polycyclic ring system; or an optionally substituted 5- or 6-membered aryl or heteroaryl residue, which optionally may be attached via a linear or branched $C_{1-8}$ alkylene group and which optionally may be fused with a saturated or unsaturated, optionally substituted mono- or polycyclic ring system;

$R^6$ denotes a linear or branched, saturated or unsaturated, optionally substituted $C_{13-30}$ aliphatic residue;

$R^7$ denotes a linear or branched, saturated or unsaturated, optionally substituted $C_{1-8}$ aliphatic residue; an unsaturated or saturated, optionally substituted 3-, 4-, 5-, 6-, 7- or 8-membered cycloaliphatic residue, which may comprise 1, 2 or 3 heteroatom(s) independently selected from the group consisting of oxygen, nitrogen and sulfur as ring member(s) and which optionally may be attached via a linear or branched $C_{1-8}$ alkylene group and optionally may be fused with a saturated or unsaturated, optionally substituted mono- or polycyclic ring system; or an optionally substituted 5- or 6-membered aryl or heteroaryl residue, which optionally may be attached via a linear or branched $C_{1-8}$ alkylene group, and which optionally may be fused with a saturated or unsaturated, optionally substituted mono- or polycyclic ring system;

$R^8$ denotes a linear or branched, saturated or unsaturated, optionally substituted $C_{1-8}$ aliphatic residue; an unsaturated or saturated, optionally substituted 3-, 4-, 5-, 6-, 7- or 8-membered cycloaliphatic residue, which may comprise 1, 2 or 3 heteroatom(s) independently selected from the group consisting of oxygen, nitrogen and sulfur as ring member(s) and which optionally may be attached via a linear or branched $C_{1-8}$ alkylene group, and which optionally may be fused with a saturated or unsaturated, optionally substituted mono- or polycyclic ring system; or an optionally substituted 5- or 6-membered aryl or heteroaryl residue, which may be fused with a saturated or unsaturated, optionally substituted mono- or polycyclic ring system and which optionally may be attached via a linear or branched $C_{1-8}$ alkylene group; and $R^9$ denotes a linear or branched, saturated or unsaturated, optionally substituted $C_{1-8}$ aliphatic residue; an unsaturated or saturated, optionally substituted 3-, 4-, 5-, 6-, 7- or 8-membered cycloaliphatic residue, which may comprise 1, 2 or 3 heteroatom(s) independently selected from the group consisting of oxygen, nitrogen and sulfur as ring member(s) and which optionally may be attached via a linear or branched $C_{1-8}$ alkylene group, and which optionally maya be fused with a saturated or unsaturated, optionally substituted mono- or polycyclic ring system; or an optionally substituted 5- or 6-membered aryl or heteroaryl residue, which optionally may be attached via a linear or branched $C_{1-8}$ alkylene group and optionally may be fused with a saturated or unsaturated, optionally substituted mono- or polycyclic ring system;

in the form of a pure stereoisomer or a mixture of stereoisomers in any mixing ratio, or a corresponding salt thereof;

wherein said $C_{1-8}$ aliphatic residues, $C_{1-12}$ aliphatic residues or $C_{13-30}$ aliphatic residues independently may be unsubstituted or optionally substituted with 1, 2, 3, 4 or 5 substituents independently selected from the group consisting of methoxy, ethoxy, n-propoxy, isopropoxy, n-butoxy, tert.-butoxy, hydroxy, halogen, —$CHF_2$, —$CH_2F$, —$CF_3$, phenyl, phenoxy, cyano, nitro, amino and di-($C_{1-3}$)-alkylamino;

said cycloaliphatic residues independently may be unsubstituted or optionally substituted with 1, 2, 3, 4 or 5 substituents independently selected from the group consisting of $C_{1-4}$ alkyl, methoxy, ethoxy, n-propoxy, iso-propoxy, n-butoxy, tert.-butoxy, hydroxy, halogen, —$CHF_2$, —$CH_2F$, —$CF_3$, phenyl, phenoxy, cyano, nitro, amino and di-($C_{1-3}$)-alkylamino;

said aryl- or heteroaryl residues independently may be unsubstituted or optionally substituted with 1, 2, 3, 4 or 5 substituents independently selected from the group consisting of methoxy, ethoxy, n-propoxy, isopropoxy, n-butoxy, tert.-butoxy, $C_{1-4}$ alkyl, hydroxy, halogen, —$CHF_2$, —$CH_2F$, —$CF_3$, phenyl, phenoxy, cyano, nitro, amino and di-($C_{1-3}$)-alkylamino;

said heteroaryl residues independently may optionally comprise 1, 2, 3, 4 or 5 heteroatom(s) as ring member(s), which are independently selected from the group consisting of oxygen, nitrogen and sulfur;

the rings of said mono- or polycyclic ring systems independently may be unsubstituted or optionally substituted with 1, 2, 3, 4 or 5 substituents independently selected from the group consisting of $C_{1-4}$ alkyl, methoxy, ethoxy, n-propoxy, isopropoxy, n-butoxy, tert.-butoxy, hydroxy, halogen, —$CHF_2$, —$CH_2F$, —$CF_3$, phenyl, phenoxy, cyano, nitro, amino and di-($CH_{1-3}$)-alkylamino; and the rings of said mono- or polycyclic ring systems are independently 5- or 6-membered and are independently saturated, unsaturated or aromatic and optionally may independently comprise 1, 2, 3, 4 or 5 heteroatom(s) as ring member(s), which are independently selected from the group consisting of oxygen, nitrogen and sulfur.

20. A compound according to claim 19, wherein:

$R^1$, $R^2$, $R^3$ and $R^4$, independently, respectively denote hydrogen, F, Cl, Br, a hydroxyl group, a cyano group, a nitro group, an amino group, a carboxy group, a —C(=O)—$R^7$ group, a —C(=O)—$OR^8$ group, an —$OR^9$ group; a residue selected from the group consisting of methyl, ethyl, n-propyl, iso-propyl, n-butyl, iso-butyl, sec-butyl, tert.-butyl, n-pentyl, iso-pentyl, neopentyl, n-hexyl, 2-hexyl, n-heptyl, n-octyl, 1,1,3,3-tetramethylbutyl, n-nonyl, n-decanol, n-uncedanyl, n-dodecanol, vinyl, propenyl, propynyl, butenyl, butynyl, pentenyl, pentynyl, hexenyl, hexynyl, octenyl and octynyl, which may optionally be substituted with 1, 2, 3, 4 or 5 substituents selected from the group consisting of methoxy, ethoxy, n-propoxy, n-butoxy, tert.-butoxy, hydroxy, F, Cl, Br, —$CHF_2$, —$CH_2F$, —$CF_3$, phenyl, phenoxy, cyano, nitro, amino, dimethylamino and diethylamino; a residue selected from the group consisting of cyclopropyl, cyclobutyl, cyclopentyl, cyclohexyl, cycloheptyl, cyclooctyl, cyclopentenyl, cyclohexenyl, cycloheptenyl and cyclooctenyl, which may optionally be substituted with 1, 2, 3, 4 or 5 substituents selected from the group consisting of methyl, ethyl, n-propyl, iso-propyl, n-butyl, sec-butyl, tert.-butyl, methoxy, ethoxy, n-propoxy, n-butoxy, tert.-butoxy, hydroxy, F, Cl, Br, —$CHF_2$, —$CH_2F$, —$CF_3$, phenyl, phenoxy, cyano, nitro, amino, dimethylamino and diethylamino; or two adjacent residues $R^1$ and $R^2$, $R^2$ and $R^3$ or $R^3$ and $R^4$, respectively, together form a 3- or 4-membered, saturated or unsaturated, aliphatic chain optionally comprising 1 or 2 heteroatom(s) selected from the group consisting of oxygen, nitrogen and sulfur as link(s), and the remaining residues $R^3$ and $R^4$, $R^1$ and $R^4$ or $R^1$ and $R^2$, respectively, denote hydrogen;

$R^5$ denotes a residue selected from the group consisting of methyl, ethyl, n-propyl, iso-propyl, n-butyl, iso-butyl, sec-butyl, tert.-butyl, n-pentyl, iso-pentyl, neopentyl, n-hexyl, 2-hexyl, n-heptyl, n-octyl, 1,1,3,3-tetramethyl -butyl, n-nonyl, n-decanol, n-uncedanyl, n-dodecanol, vinyl, propenyl, propynyl, butenyl, butynyl, pentenyl, pentynyl, hexenyl, hexynyl, octenyl and octynyl, which may optionally be substituted with 1, 2, 3, 4 or 5 substituents selected from the group consisting of methoxy, ethoxy, n-propoxy, n-butoxy, tert.-butoxy, hydroxy, F, Cl, Br, —$CHF_2$, —$CH_2F$, —$CF_3$, phenyl, phenoxy, cyano, nitro, amino, dimethylamino and diethylamino; a residue selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, imidazolidinyl, tetrahydrofuranyl (tetrahydrofuryl), piperidinyl, piperazinyl and morpholinyl, which may optionally be substituted with 1, 2, 3, 4 or 5 substituents selected from the group consisting of methyl, ethyl, n-propyl, iso-propyl, n-butyl, sec-butyl, tert.-butyl, methoxy, ethoxy, n-propoxy, n-butoxy, tert.-butoxy, hydroxy, F, Cl, Br, —$CHF_2$, —$CH_2F$, —$CF_3$, phenyl, phenoxy, cyano, nitro, amino, dimethylamino and diethylamino; or a residue selected from the group consisting of phenyl, naphthyl, pyrrolyl, indolyl, furyl, benzo[b]furanyl, thienyl, benzo[b]thienyl, pyrazolyl, imidazolyl, thiazolyl, thiadiazolyl, triazolyl, oxazolyl, isoxazolyl, pyridinyl, pyridazinyl, pyrimidinyl, pyrazinyl, pyranyl, indazolyl, purinyl, indolizinyl, quinolinyl, isoquinolinyl and quinazolinyl, which may optionally be substituted with 1, 2, 3, 4 or 5 substituents selected from the group consisting of methyl, ethyl, n-propyl, iso-propyl, n-butyl, sec-butyl, tert.-butyl, methoxy, ethoxy, n-propoxy, n-butoxy, tert.-butoxy, hydroxy, F, Cl, Br, —$CHF_2$, —$CH_2F$, —$CF_3$, phenyl, phenoxy, cyano, nitro, amino, dimethylamino and diethylamino;

$R^6$ denotes a residue selected from the group consisting of n-tridecanyl, n-tetradecanyl, n-pentadecanyl, n-hexadecanyl, n-heptadecanyl, n-octadecanyl, n-nonadecanyl, n-eicosanyl, (3,13)-dimethylhexadecanyl, (5,9)-dimethylhexadecanyl, 2-methylheptadecanyl, 5-methylheptadecanyl, 7-methylheptadecanyl, (3,12)-dimethylheptadecanyl, (5,11)-dimethylheptadecanyl, (7,11)-dimethylheptadecanyl and 2-methyloctadecanyl, which optionally may be substituted with 1, 2, 3, 4 or 5 substituents selected from the group consisting of methoxy, ethoxy, n-propoxy, n-butoxy, tert.-butoxy, hydroxy, F, Cl, Br, —$CHF_2$, —$CH_2F$, —$CF_3$, phenyl, phenoxy, cyano, nitro, amino, dimethylamino and diethylamino;

$R^7$ denotes a residue selected from the group consisting of methyl, ethyl, n-propyl, iso-propyl, n-butyl, iso-butyl, sec-butyl, tert.-butyl, n-pentyl, iso-pentyl, neopentyl and n-hexyl, which optionally may be substituted with 1, 2, 3, 4 or 5 substituents selected from the group consisting of methoxy, ethoxy, n-propoxy, n-butoxy, tert.-butoxy, hydroxy, F, Cl, Br, —$CHF_2$, —$CH_2F$, —$CF_3$, phenyl, phenoxy, cyano, nitro, amino, dimethylamino and diethylamino; a residue selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, imidazolidinyl, tetrahydrofuranyl, piperidinyl, piperazinyl and morpholinyl, which optionally may be substituted with 1, 2, 3, 4 or 5 substituents selected from the group consisting of methyl, ethyl, n-propyl, iso-propyl, n-butyl, sec-butyl, tert.-butyl, methoxy, ethoxy, n-propoxy, n-butoxy, tert.- butoxy, hydroxy, F, Cl, Br, —CHF$_2$, —CH$_2$F, —CF$_3$, phenyl, phenoxy, cyano, nitro, amino, dimethylamino and diethylamino; or a residue selected from the group consisting of phenyl, naphthyl, pyrrolyl, indolyl, furyl, benzo[b]furanyl, thienyl, benzo[b]thienyl, pyrazolyl, imidazolyl, thiazolyl, thiadiazolyl, triazolyl, oxazolyl, isoxazolyl and pyridinyl, which optionally may be substituted with 1, 2, 3, 4 or 5 substituents selected from the group consisting of methyl, ethyl, n-propyl, iso-propyl, n-butyl, sec-butyl, tert.-butyl, methoxy, ethoxy, n-propoxy, n-butoxy, tert.-butoxy, hydroxy, F, Cl, Br, —CHF$_2$, —CH$_2$F, —CF$_3$, phenyl, phenoxy, cyano, nitro, amino, dimethylamino and diethylamino;

$R^8$ denotes a residue selected from the group consisting of methyl, ethyl, n-propyl, iso-propyl, n-butyl, iso-butyl, sec-butyl, tert.-butyl, n-pentyl, iso-pentyl, neopentyl and n-hexyl, which optionally may be substituted with 1, 2, 3, 4 or 5 substituents selected from the group consisting of methoxy, ethoxy, n-propoxy, n-butoxy, tert.-butoxy, hydroxy, F, Cl, Br, —CHF$_2$, —CH$_2$F, —CF$_3$, phenyl, phenoxy, cyano, nitro, amino, dimethylamino and diethylamino; a residue selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, imidazolidinyl, tetrahydrofuranyl, piperidinyl, piperazinyl and morpholinyl, which optionally may be substituted with 1, 2, 3, 4 or 5 substituents selected from the group consisting of methyl, ethyl, n-propyl, iso-propyl, n-butyl, sec-butyl, tert.-butyl, methoxy, ethoxy, n-propoxy, n-butoxy, tert.-butoxy, hydroxy, F, Cl, Br, —CHF$_2$, —CH$_2$F, —CF$_3$, phenyl, phenoxy, cyano, nitro, amino, dimethylamino and diethylamino; or a residue selected from the group consisting of phenyl, naphthyl, pyrrolyl, indolyl, furyl, benzo[b]furanyl, thienyl, benzo[b]thienyl, pyrazolyl, imidazolyl, thiazolyl, thiadiazolyl, triazolyl, oxazolyl, isoxazolyl and pyridinyl, which optionally may be substituted with 1, 2, 3, 4 or 5 substituents selected from the group consisting of methyl, ethyl, n-propyl, iso-propyl, n-butyl, sec-butyl, tert.-butyl, methoxy, ethoxy, n-propoxy, n-butoxy, tert.-butoxy, hydroxy, F, Cl, Br, —CHF$_2$, —CH$_2$F, —CF$_3$, phenyl, phenoxy, cyano, nitro, amino, dimethylamino and diethylamino; and $R^9$ denotes a residue selected from the group consisting of methyl, ethyl, n-propyl, iso-propyl, n-butyl, iso-butyl, sec-butyl, tert.-butyl, n-pentyl, iso-pentyl, neopentyl and n-hexyl, which optionally may be substituted with 1, 2, 3, 4 or 5 substituents selected from the group consisting of methoxy, ethoxy, n-propoxy, n-butoxy, tert.-butoxy, hydroxy, F, Cl, Br, —CHF$_2$, —CH$_2$F, —CF$_3$, phenyl, phenoxy, cyano, nitro, amino, dimethylamino and diethylamino; a residue selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, imidazolidinyl, tetrahydrofuranyl, piperidinyl, piperazinyl and morpholinyl, which optionally may be substituted with 1, 2, 3, 4 or 5 substituents selected from the group consisting of methyl, ethyl, n-propyl, iso-propyl, n-butyl, sec-butyl, tert.-butyl, methoxy, ethoxy, n-propoxy, n-butoxy, tert.-butoxy, hydroxy, F, Cl, Br, —CHF$_2$, —CH$_2$F, —CF$_3$, phenyl, phenoxy, cyano, nitro, amino, dimethylamino and diethylamino; or a residue selected from the group consisting of phenyl, naphthyl, pyrrolyl, indolyl, furyl, benzo[b]furanyl, thienyl, benzo[b]thienyl, pyrazolyl, imidazolyl, thiazolyl, thiadiazolyl, triazolyl, oxazolyl, isoxazolyl and pyridinyl, which may optionally be substituted with 1, 2, 3, 4 or 5 substituents selected from the group consisting of methyl, ethyl, n-propyl, iso-propyl, n-butyl, sec-butyl, tert.-butyl, methoxy, ethoxy, n-propoxy, n-butoxy, tert.-butoxy, hydroxy, F, Cl, Br, —CHF$_2$, —CH$_2$F, —CF$_3$, phenyl, phenoxy, cyano, nitro, amino, dimethylamino and diethylamino.

21. A compound according to claim 19, wherein:

$R^1$, $R^2$, $R^3$ and $R^4$, independently, respectively denote hydrogen, F, Cl, Br, or a residue selected from the group consisting of methyl, ethyl, n-propyl, iso-propyl, n-butyl, iso-butyl, sec-butyl, tert.-butyl, n-pentyl, iso-pentyl and neopentyl;

$R^5$ denotes a residue selected from the group consisting of phenyl, naphthyl, 2-furyl, 3-furyl, 2-thienyl, 3-thienyl, 2-pyridyl, 3-pyridyl and 4-pyridyl; and $R^6$ denotes a residue selected from the group consisting of n-tridecanyl, n-tetradecanyl, n-pentadecanyl, n-hexadecanyl, n-heptadecanyl, n-octadecanyl, n-nonadecanyl, n-eicosanyl, (3,13)-dimethylhexadecanyl, (5,9)-dimethylhexadecanyl, 2-methylheptadecanyl, 5-methylheptadecanyl, 7-methylheptadecanyl, (3,12)-dimethylheptadecanyl, (5,11)-dimethylheptadecanyl, (7,11)-dimethylheptadecanyl and 2-methyloctadecanyl.

22. A compound according to claim 1, selected from the group consisting of:

hexadecyl-(6-methyl-2-pyridin-2-yl-imidazo[1,2-a]-pyridin-3-yl)-amine, (6,8-dichloro-2-thiophen-3-yl-imidazo[1,2-a]pyridin-3-yl)-hexadecyl-amine, corresponding salts thereof.

23. A process for producing a substituted imidazo[1,2-a] pyridine compound according to claim 1, said process comprising reacting an aminopyridine corresponding to formula II:

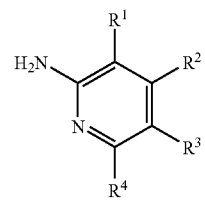

II wherein $R^1$ to $R^4$ have the meanings given in claim 1, with an aldehyde corresponding to formula III:

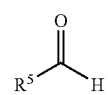

III wherein $R^5$ has the meaning given in claim 1, and with an isonitrile corresponding to formula IV

IV, wherein $R^6$ has the meaning given in claim 1, to obtain a resulting substituted imidazo[1,2-a]pyridine compound, and optionally isolating or purifying the resulting compound.

24. A pharmaceutical composition comprising a substituted imidazo[1,2-a]pyridine compound according to claim 1 and at least one physiologically acceptable auxiliary substance.

25. A method of treating or inhibiting pain VR1 or CB1 receptors in a mammal, said method comprising administering to said mammal an effective amount of a compound according to claim 1.

26. A method according to claim 25, wherein said pain comprises neuropathic pain or cluster headaches.

27. A method according to claim 25, wherein said pain is migraine.

28. A method according to claim 25, wherein said substituted imidazo[1,2-a]pyridine compound is a compound corresponding to formula (Ia):

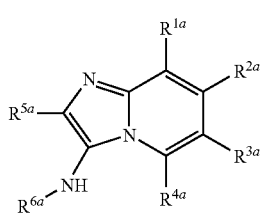

(Ia)

wherein $R^{1a}$, $R^{2a}$, $R^{3a}$ and $R^{4a}$ may be identical or different and respectively denote hydrogen, halogen, a hydroxy group, a cyano group, a nitro group, an amino group, a carboxy group, a —C(=O)—$R^{7a}$ group, a —(C=O)—$OR^{8a}$ group, an $OR^{9a}$ group; a linear or branched, saturated or unsaturated, optionally at least monosubstituted aliphatic residue; a saturated or unsaturated, optionally at least monosubstituted cycloaliphatic residue optionally attached via an alkylene group; or two adjacent residues $R^{1a}$ and $R^{2a}$, $R^{2a}$ and $R^{3a}$ or $R^{3a}$ and $R^{4a}$, respectively, together form a 3- or 4-membered, saturated or unsaturated, aliphatic ring optionally comprising at least one heteroatom as a ring member, and the remaining residues $R^{3a}$ and $R^{4a}$, $R^{1a}$ and $R^{4a}$ or $R^{1a}$ and $R^{2a}$, respectively, each denote hydrogen;

$R^{5a}$ denotes a linear or branched, saturated or unsaturated, optionally at least monosubstituted aliphatic residue; a saturated or unsaturated, optionally at least monosubstituted cycloaliphatic residue optionally comprising at least one heteroatom as a ring member, wherein said cycloaliphatic residue optionally may be attached via an alkylene group and optionally may be fused with an optionally at least monosubstituted, mono- or polycyclic ring system; an optionally at least monosubstituted phenyl residue optionally attached via an alkylene group, wherein said phenyl residue optionally may be fused with an optionally at least monosubstituted, mono- or polycyclic ring system; wherein the optional substituents of the phenyl residue or the mono- or polycyclic ring system are selected from the group consisting of $C_{1-4}$ alkoxy, $C_{1-4}$ alkyl, hydroxy, halogen, —$CHF_2$, —$CH_2F$, —$CF_3$, phenyl, phenoxy, cyano, nitro, amino and di-($C_{1-3}$)-alkylamino; or an optionally at least monosubstituted heteroaryl residue optionally attached via an alkylene group, wherein said heteroaryl residue optionally may be fused with an optionally at least monosubstituted, mono- or polycyclic ring system;

$R^{6a}$ denotes a linear or branched, saturated or unsaturated, optionally at least monosubstituted aliphatic residue with 1 to 12 carbon atoms;

$R^{7a}$ denotes a linear or branched, saturated or unsaturated, optionally at least monosubstituted aliphatic residue; a saturated or unsaturated, optionally at least monosubstituted cycloaliphatic residue optionally comprising at least one heteroatom as a ring member, wherein said cycloaliphatic residue optionally may be attached via an alkylene group and optionally may be fused with an optionally at least monosubstituted, mono- or polycyclic ring system; or an optionally at least monosubstituted aryl or heteroaryl residue optionally attached via an alkylene group, wherein said aryl or heteroaryl residue optionally may be fused with an optionally at least monosubstituted, mono- or polycyclic ring system;

$R^{8a}$ denotes a linear or branched, saturated or unsaturated, optionally at least monosubstituted aliphatic residue; a saturated or unsaturated, optionally at least monosubstituted cycloaliphatic residue optionally comprising at least one heteroatom as a ring member, wherein said cycloaliphatic residue optionally may be attached via an alkylene group and optionally may be fused with an optionally at least monosubstituted, mono- or polycyclic ring system; or an optionally at least monosubstituted aryl or heteroaryl residue optionally attached via an alkylene group, wherein said aryl or heteroaryl residue optionally may be fused with an optionally at least monosubstituted, mono- or polycyclic ring system; and $R^{9a}$ denotes a linear or branched, saturated or unsaturated, optionally at least monosubstituted aliphatic residue; a saturated or unsaturated, optionally at least monosubstituted cycloaliphatic residue optionally comprising at least one heteroatom as a ring member, wherein said cycloaliphatic residue optionally may be attached via an alkylene group and optionally may be fused with an optionally at least monosubstituted, mono- or polycyclic ring system; or an optionally at least monosubstituted aryl or heteroaryl residue optionally attached via an alkylene group, wherein said aryl or heteroaryl residue optionally may be fused with an optionally at least monosubstituted, mono- or polycyclic ring system.

29. A method according to claim 28, wherein $R^{1a}$, $R^{2a}$, $R^{3a}$ and $R^{4a}$ may be identical or different and respectively denote hydrogen, halogen, a hydroxy group, a cyano group, a nitro group, an amino group, a carboxy group, a —C(=O)—$R^{7a}$ group, a —(C=O)—$OR^{8a}$ group, an $OR^{9a}$ group; a linear or branched, saturated or unsaturated, optionally at least monosubstituted aliphatic $C_{1-12}$ residue; a saturated or unsaturated, optionally at least monosubstituted cycloaliphatic $C_{3-8}$ residue optionally attached via a $C_{1-8}$ alkylene group; or two adjacent residues $R^{1a}$ and $R^{2a}$, $R^{2a}$ and $R^{3a}$ or $R^{3a}$ and $R^{4a}$, respectively, together form a 3- or 4-membered, saturated or unsaturated, aliphatic ring optionally comprising at least one heteroatom as a ring member, and the remaining residues $R^{3a}$ and $R^{4a}$, $R^{1a}$ and $R^{4a}$ or $R^{1a}$ and $R^{2a}$, respectively, each denote hydrogen.

30. A method according to claim 29, wherein $R^{1a}$, $R^{2a}$, $R^{3a}$ and $R^{4a}$ may be identical or different and respectively denote hydrogen, F, Cl, Br, a hydroxy group, a carboxy group, a —C(=O)—$R^{7a}$ group, a —(C=O)—$OR^{8a}$ group, an $OR^{9a}$ group or a linear or branched $C_{1-12}$ alkyl residue.

31. A method according to claim 28, wherein $R^{5a}$ denotes a linear or branched, saturated or unsaturated, optionally at least monosubstituted aliphatic $C_{1-12}$ residue; a saturated or unsaturated, optionally at least monosubstituted cycloaliphatic $C_{3-8}$ residue optionally comprising at least one heteroatom as a ring member, wherein said cycloaliphatic residue optionally may be attached via a $C_{1-8}$ alkylene group and optionally may be fused with an optionally at least monosubstituted, mono- or polycyclic ring system; an optionally at least monosubstituted phenyl residue optionally attached via a $C_{1-8}$ alkylene group, wherein said phenyl residue optionally may be fused with an optionally at least monosubstituted, mono- or polycyclic ring system; wherein the optionally substituents on the phenyl residue or the mono- or polycyclic ring system are selected from the group consisting of $C_{1-4}$ alkoxy, $C_{1-4}$ alkyl, hydroxy, halogen, —$CHF_2$, —$CH_2F$, —$CF_3$, phenyl, phenoxy, cyano, nitro, amino and di-$(C_{1-3})$-alkylamino; or an optionally at least monosubstituted 5- or 6-membered heteroaryl residue optionally attached via a $C_{1-8}$ alkylene group, wherein said heteroaryl residue optionally may be fused with an optionally at least monosubstituted, mono- or polycyclic ring system.

32. A method according to claim 31, wherein $R^{5a}$ denotes a linear or branched $C_{1-8}$ alkyl residue; a saturated or unsaturated, optionally at least monosubstituted cycloaliphatic $C_{3-8}$ residue optionally comprising at least one heteroatom as a ring member, wherein said cycloaliphatic residue optionally may be attached via a $C_{1-3}$ alkylene group; an optionally at least monosubstituted phenyl residue optionally attached via a $C_{1-3}$ alkylene group, wherein said phenyl residue optionally may be fused with an optionally at least monosubstituted, mono- or polycyclic ring system; and wherein the optional substituents on the phenyl residue or the mono- or polycyclic ring system are selected from the group consisting of $C_{1-4}$ alkoxy, $C_{1-4}$ alkyl, hydroxy, halogen, —$CHF_2$, —$CH_2F$, —$CF_3$, phenyl, phenoxy, cyano, nitro, amino and di-$(C_{1-3})$-alkylamino; or an at least monosubstituted, 5- or 6-membered heteroaryl residue optionally attached via a $C_{1-3}$ alkylene group.

33. A method according to claim 32, wherein $R^{5a}$ denotes a residue selected from the group consisting of optionally at least monosubstituted phenyl; optionally at least monosubstituted furyl; optionally at least monosubstituted thienyl, and optionally at least monosubstituted pyridyl, wherein the substituents on the phenyl, furyl, thienyl or pyridyl group are independently selected from the group consisting of $C_{1-4}$ alkoxy, $C_{1-4}$ alkyl, hydroxy, halogen, —$CHF_2$, —$CH_2F$, —$CF_3$, phenyl, phenoxy, cyano, nitro, amino and di-$(C_{1-3})$-alkylamino.

34. A method according to claim 28, wherein $R^{6a}$ denotes a linear or branched, optionally at least monosubstituted $C_{1-12}$ alkyl residue, a —$(CH_2)$-phenyl group, a —$C(CH_3)_2$—$(CH_2)_{0-8}$—$CH_3$ group or a 1,1,3,3-tetramethylbutyl group.

35. A method according to claim 34, wherein $R^{6a}$ denotes a —$(CH_2)_6$—$CH_3$ group, a —$(CH_2)_7$—$CH_3$ group, a —$(CH_2)_8$—$CH_3$ group, a —$(CH_2)$ phenyl group, a —$C(CH_3)_2$—$(CH_2)_4$—$CH_3$ group, a —$C(CH_3)_2$—$(CH_2)_5$—$CH_3$ group, a —$C(CH_3)_2$—$(CH_2)_6$—$CH_3$ group, or a 1,1,3,3-tetramethylbutyl group.

36. A method according to claim 30, wherein $R^{7a}$ denotes a linear or branched, saturated or unsaturated, optionally at least monosubstituted aliphatic $C_{1-8}$ residue; a saturated or unsaturated, optionally at least monosubstituted cycloaliphatic $C_{3-8}$ residue optionally comprising at least one heteroatom as a ring member, wherein said cycloaliphatic residue optionally may be attached via a $C_{1-8}$ alkylene group and optionally may be fused with an optionally at least monosubstituted, mono- or polycyclic ring system; or an optionally at least monosubstituted, 5- or 6-membered aryl or heteroaryl residue optionally attached via a $C_{1-8}$ alkylene group, wherein said aryl or heteroaryl residue optionally may be fused with an optionally at least monosubstituted, mono- or polycyclic ring system.

37. A method according to claim 36, wherein $R^{7a}$ denotes a linear or branched $C_{1-4}$ alkyl residue; a saturated or unsaturated, optionally at least monosubstituted cycloaliphatic $C_{3-8}$ residue optionally comprising at least one heteroatom as a ring member, wherein said cycloaliphatic residue optionally may be attached via a $C_{1-3}$ alkylene group; or an optionally at least monosubstituted, 5- or 6-membered aryl or heteroaryl residue optionally attached via a $C_{1-3}$ alkylene group, wherein said aryl or heteroaryl residue optionally may be fused with an optionally at least monosubstituted, mono- or polycyclic ring system.

38. A method according to claim 28, wherein $R^{8a}$ denotes a linear or branched, saturated or unsaturated, optionally at least monosubstituted aliphatic $C_{1-8}$ residue; a saturated or unsaturated, optionally at least monosubstituted cycloaliphatic $C_{3-8}$ residue optionally comprising at least one heteroatom as a ring member, wherein said cycloaliphatic residue optionally may be attached via a $C_{1-8}$ alkylene group and optionally may be fused with an optionally at least monosubstituted, mono- or polycyclic ring system; or an optionally at least monosubstituted, 5- or 6-membered aryl or heteroaryl residue optionally attached via a $C_{1-8}$ alkylene group, wherein said aryl or heteroaryl residue optionally may be fused with an optionally at least monosubstituted, mono- or polycyclic ring system.

39. A method according to claim 38, wherein $R^{8a}$ denotes a linear or branched $C_{1-4}$ alkyl residue; a saturated or unsaturated, optionally at least monosubstituted cycloaliphatic $C_{3-8}$ residue optionally comprising at least one heteroatom as a ring member, wherein said cycloaliphatic residue optionally maya be attached via a $C_{1-3}$ alkylene group; or an optionally at least monosubstituted, 5- or 6-membered aryl or heteroaryl residue optionally attached via a $C_{1-3}$ alkylene group, wherein said aryl or heteroaryl residue optionally may be fused with an optionally at least monosubstituted, mono- or polycyclic ring system.

40. A method according to claim 28, wherein $R^{9a}$ denotes a linear or branched, saturated or unsaturated, optionally at least monosubstituted aliphatic $C_{1-8}$ residue; a saturated or unsaturated, optionally at least monosubstituted cycloaliphatic $C_{3-8}$ residue optionally comprising at least one heteroatom as a ring member, wherein said cycloaliphatic residue optionally may be attached via a $C_{1-8}$ alkylene group and optionally may be fused with an optionally at least monosubstituted, mono- or polycyclic ring system; or an optionally at least monosubstituted, 5- or 6-membered aryl or heteroaryl residue optionally attached via a $C_{1-8}$ alkylene group, wherein said aryl or heteroaryl residue optionally may be fused with an optionally at least monosubstituted, mono- or polycyclic ring system.

41. A method according to claim 40, wherein $R^{9a}$ denotes a linear or branched $C_{1-4}$ alkyl residue; a saturated or unsaturated, optionally at least monosubstituted cycloaliphatic $C_{3-8}$ residue optionally comprising at least one heteroatom as a ring member, wherein said cycloaliphatic residue optionally may be attached via a $C_{1-3}$ alkylene group; or an optionally at least monosubstituted, 5- or 6-membered aryl or heteroaryl residue optionally attached via a $C_{1-3}$ alkylene group, wherein said aryl or heteroaryl residue optionally may be fused with an optionally at least monosubstituted, mono- or polycyclic ring system.

42. A method according to claim 28, wherein:
$R^{1a}$, $R^{2a}$, $R^{3a}$ and $R^{4a}$ independently, respectively denote hydrogen, halogen, a hydroxy group, a cyano group, a nitro group, an amino group, a carboxy group, a —$C(=O)$—$R^{7a}$ group, a —$C(=O)$—$OR^{8a}$ group, an —$OR^{9a}$ group; a linear or branched, saturated or unsaturated, optionally substituted $C_{1-12}$ aliphatic residue; an unsaturated or saturated, optionally substituted 3-, 4-, 5-, 6-, 7- or 8-membered cycloaliphatic residue, which may be attached via a linear or branched $C_{1-8}$ alkylene group; or two adjacent residues $R^{1a}$ and $R^{2a}$, $R^{2a}$ and $R^{3a}$ or $R^{3a}$ and $R^{4a}$, respectively, together form a 3- or 4-membered, saturated or unsaturated, aliphatic ring optionally comprising 1 or 2 heteroatom(s) selected from the group consisting of oxygen, nitrogen and sulfur as ring members, and the remaining residues $R^{3a}$ and $R^{4a}$, $R^{1a}$ and $R^{4a}$ or $R^{1a}$ and $R^{2a}$, respectively, each denote hydrogen;

$R^5$ denotes a linear or branched, saturated or unsaturated, optionally substituted $C_{1-12}$ aliphatic residue; an unsaturated or saturated, optionally substituted 3-, 4-, 5-, 6-, 7- or 8-membered cycloaliphatic residue, which may comprise 1, 2 or 3 heteroatom(s) independently selected from the group consisting of oxygen, nitrogen and sulfur as ring member(s) and which optionally may be attached via a linear or branched $C_{1-8}$ alkylene group and optionally may be fused with a saturated or unsaturated, optionally substituted mono- or polycyclic ring system; or an optionally substituted 5- or 6-membered aryl or heteroaryl residue, which may be fused with a saturated or unsaturated, optionally substituted mono- or polycyclic ring system and/or attached via a linear or branched $C_{1-8}$ alkylene group;

$R^{6a}$ denotes a linear or branched, saturated or unsaturated, optionally substituted $C_{1-12}$ aliphatic residue;

$R^{7a}$ denotes a linear or branched, saturated or unsaturated, optionally substituted $C_{1-8}$ aliphatic residue; an unsaturated or saturated, optionally substituted 3-, 4-, 5-, 6-, 7- or 8-membered cycloaliphatic residue, which may comprise 1, 2 or 3 heteroatom(s) mutually independently selected from the group consisting of oxygen, nitrogen and sulfur as ring member(s) and/or may be attached via a linear or branched $C_{1-8}$ alkylene group and/or fused with a saturated or unsaturated, optionally substituted mono- or polycyclic ring system; or an optionally substituted 5- or 6-membered aryl or heteroaryl residue, which may be fused with a saturated or unsaturated, optionally substituted mono- or polycyclic ring system and/or attached via a linear or branched $C_{1-8}$ alkylene group;

$R^{8a}$ denotes a linear or branched, saturated or unsaturated, optionally substituted $C_{1-8}$ aliphatic residue; an unsaturated or saturated, optionally substituted 3-, 4-, 5-, 6-, 7- or 8-membered cycloaliphatic residue, which may comprise 1, 2 or 3 heteroatom(s) mutually independently selected from the group consisting of oxygen, nitrogen and sulfur as ring member(s) and/or may be attached via a linear or branched $C_{1-8}$ alkylene group and/or fused with a saturated or unsaturated, optionally substituted mono- or polycyclic ring system; or an optionally substituted 5- or 6-membered aryl or heteroaryl residue, which may be fused with a saturated or unsaturated, optionally substituted mono- or polycyclic ring system and/or attached via a linear or branched $C_{1-8}$ alkylene group; and $R^{9a}$ denotes a linear or branched, saturated or unsaturated, optionally substituted $C_{1-8}$ aliphatic residue; an unsaturated or saturated, optionally substituted 3-, 4-, 5-, 6-, 7- or 8-membered cycloaliphatic residue, which may comprise 1, 2 or 3 heteroatom(s) mutually independently selected from the group consisting of oxygen, nitrogen and sulfur as ring member(s) and/or may be attached via a linear or branched $C_{1-8}$ alkylene group and/or fused with a saturated or unsaturated, optionally substituted mono- or polycyclic ring system; or an optionally substituted 5- or 6-membered aryl or heteroaryl residue, which may be fused with a saturated or unsaturated, optionally substituted mono- or polycyclic ring system and/or attached via a linear or branched $C_{1-8}$ alkylene group;

in the form of a pure stereoisomer or a mixture of stereoisomers in any mixing ratio, or a corresponding salt thereof;

wherein said $C_{1-8}$ aliphatic residues or $C_{1-12}$ aliphatic residues independently may be unsubstituted or optionally substituted with 1, 2, 3, 4 or 5 substituents independently selected from the group consisting of methoxy, ethoxy, n-propoxy, isopropoxy, n-butoxy, tert.-butoxy, hydroxy, halogen, —$CHF_2$, —$CH_2F$, —$CF_3$, phenyl, phenoxy, cyano, nitro, amino and di-$(C_{1-3})$-alkylamino;

said cycloaliphatic residues may be unsubstituted or optionally substituted with 1, 2, 3, 4 or 5 substituents independently selected from the group consisting of $C_{1-4}$ alkyl, methoxy, ethoxy, n-propoxy, isopropoxy, n-butoxy, tert.-butoxy, hydroxy, halogen, —$CHF_2$, —$CH_2F$, —$CF_3$, phenyl, phenoxy, cyano, nitro, amino and di-$(C_{1-3})$-alkylamino;

said aryl- or heteroaryl residues may be unsubstituted or optionally substituted with 1, 2, 3, 4 or 5 substituents independently selected from the group consisting of methoxy, ethoxy, n-propoxy, isopropoxy, n-butoxy, tert.-butoxy, $C_{1-4}$ alkyl, hydroxy, halogen, —$CHF_2$, —$CH_2F$, —$CF_3$, phenyl, phenoxy, cyano, nitro, amino and di-$(C_{1-3})$-alkylamino;

said heteroaryl residues optionally may comprise 1, 2, 3, 4 or 5 heteroatom(s) as ring member(s) independently selected from the group consisting of oxygen, nitrogen and sulfur;

the rings of said mono- or polycyclic ring systems may be unsubstituted or optionally substituted with 1, 2, 3, 4 or 5 substituents independently selected from the group consisting of $C_{1-4}$ alkyl, methoxy, ethoxy, n-propoxy, isopropoxy, n-butoxy, tert.-butoxy, hydroxy, halogen, —$CHF_2$, —$CH_2F$, —$CF_3$, phenyl, phenoxy, cyano, nitro, amino and di-$(C_{1-3})$-alkylamino; and the rings of said mono- or polycyclic ring systems are each 5- or 6-membered and are independently saturated, unsaturated or aromatic and optionally may comprise 1, 2, 3, 4 or 5 heteroatom(s) as ring member(s) independently selected from the group consisting of oxygen, nitrogen and sulfur.

43. A method according to claim 42, wherein:

$R^{1a}$, $R^{2a}$, $R^{3a}$ and $R^{4a}$, independently, respectively denote hydrogen, F, Cl, Br, a hydroxy group, a cyano group, a nitro group, an amino group, a carboxy group, a —C(=O)—$R^{7a}$ group, a —C(=O)—$OR^{8a}$ group, an —$OR^{9a}$ group; a residue selected from the group consisting of methyl, ethyl, n-propyl, iso-propyl, n-butyl, iso-butyl, sec-butyl, tert.-butyl, n-pentyl, iso-pentyl, neopentyl, n-hexyl, 2-hexyl, n-heptyl, n-octyl, 1,1,3,3-tetramethylbutyl, n-nonyl, n-decanol, n-uncedanyl, n-dodecanol, vinyl, propenyl, propynyl, butenyl, butynyl, pentenyl, pentynyl, hexenyl, hexynyl, octenyl and octynyl, which may optionally be substituted with 1, 2, 3, 4 or 5 substituents selected from the group consisting of methoxy, ethoxy, n-propoxy, n-butoxy, tert.-butoxy, hydroxy, F, Cl, Br, —$CHF_2$, —$CH_2F$, —$CF_3$, phenyl, phenoxy, cyano, nitro, amino, dimethylamino and diethylamino; a residue selected from the group consisting of cyclopropyl, cyclobutyl, cyclopentyl, cyclohexyl, cycloheptyl, cyclooctyl, cyclopentenyl, cyclohexenyl, cycloheptenyl and cyclooctenyl, which may optionally be substituted with 1, 2, 3, 4 or 5 substituents selected from the group consisting of methyl, ethyl, n-propyl, iso-propyl, n-butyl, sec-butyl, tert.-butyl, methoxy, ethoxy, n-propoxy, n-butoxy, tert.-butoxy, hydroxy, F, Cl, Br, —CHF$_2$, —CH$_2$F, —CF$_3$, phenyl, phenoxy, cyano, nitro, amino, dimethylamino and diethylamino; or two adjacent residues R$^{1a}$ and R$^{2a}$, R$^{2a}$ and R$^{3a}$ or R$^{3a}$ and R$^{4a}$, respectively, together form a 3- or 4-membered, saturated or unsaturated, aliphatic ring member optionally comprising 1 or 2 heteroatom(s) selected from the group consisting of oxygen, nitrogen and sulfur as ring members, and the remaining residues R$^{3a}$ and R$^{4a}$, R$^{1a}$ and R$^{4a}$ or R$^{1a}$ and R$^{2a}$, respectively each denote hydrogen;

R$^{5a}$ denotes a residue selected from the group consisting of methyl, ethyl, n-propyl, iso-propyl, n-butyl, iso-butyl, sec-butyl, tert.-butyl, n-pentyl, iso-pentyl, neopentyl, n-hexyl, 2-hexyl, n-heptyl, n-octyl, 1,1,3,3-tetramethylbutyl, n-nonyl, n-decanol, n-uncedanyl, n-dodecanol, vinyl, propenyl, propynyl, butenyl, butynyl, pentenyl, pentynyl, hexenyl, hexynyl, octenyl and octynyl, which may optionally be substituted with 1, 2, 3, 4 or 5 substituents selected from the group consisting of methoxy, ethoxy, n-propoxy, n-butoxy, tert.-butoxy, hydroxy, F, Cl, Br, —CHF$_2$, —CH$_2$F, —CF$_3$, phenyl, phenoxy, cyano, nitro, amino, dimethylamino and diethylamino; a residue selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, imidazolidinyl, tetrahydrofuranyl (tetrahydrofuryl), piperidinyl, piperazinyl and morpholinyl, which may optionally be substituted with 1, 2, 3, 4 or 5 substituents selected from the group consisting of methyl, ethyl, n-propyl, iso-propyl, n-butyl, sec-butyl, tert.-butyl, methoxy, ethoxy, n-propoxy, n-butoxy, tert.-butoxy, hydroxy, F, Cl, Br, —CHF$_2$, —CH$_2$F, —CF$_3$, phenyl, phenoxy, cyano, nitro, amino, dimethylamino and diethylamino; or a residue selected from the group consisting of phenyl, naphthyl, pyrrolyl, indolyl, furyl (furanyl), benzo[b]furanyl, thienyl (thiophenyl), benzo[b]thienyl, pyrazolyl, imidazolyl, thiazolyl, thiadiazolyl, triazolyl, oxazolyl, isoxazolyl, pyridinyl, pyridazinyl, pyrimidinyl, pyrazinyl, pyranyl, indazolyl, purinyl, indolizinyl, quinolinyl, isoquinolinyl and quinazolinyl, which may optionally be substituted with 1, 2, 3, 4 or 5 substituents selected from the group consisting of methyl, ethyl, n-propyl, iso-propyl, n-butyl, sec-butyl, tert.-butyl, methoxy, ethoxy, n-propoxy, n-butoxy, tert.-butoxy, hydroxy, F, Cl, Br, —CHF$_2$, —CH$_2$F, —CF$_3$, phenyl, phenoxy, cyano, nitro, amino, dimethylamino and diethylamino;

R$^{6a}$ denotes a residue selected from the group consisting of methyl, ethyl, n-propyl, n-butyl, n-pentyl, n-hexyl, n-heptyl, n-octyl, n-nonyl, n-decanol, n-undecanyl and n-dodecanol, which may optionally be substituted with 1, 2, 3, 4 or 5 substituents selected from the group consisting of methoxy, ethoxy, n-propoxy, n-butoxy, tert.-butoxy, hydroxy, F, Cl, Br, —CHF$_2$, —CH$_2$F, —CF$_3$, phenyl, phenoxy, cyano, nitro, amino, dimethylamino and diethylamino; a —C(CH$_3$)$_2$—(CH$_2$)$_m$—CH$_3$ group with m=0, 1, 2, 3, 4, 5, 6, 7 or 8, or a 1,1,3,3-tetramethylbutyl group;

R$^{7a}$ denotes a residue selected from the group consisting of methyl, ethyl, n-propyl, iso-propyl, n-butyl, iso-butyl, sec-butyl, tert.-butyl, n-pentyl, iso-pentyl, neopentyl and n-hexyl, which may optionally be substituted with 1, 2, 3, 4 or 5 substituents selected from the group consisting of methoxy, ethoxy, n-propoxy, n-butoxy, tert.-butoxy, hydroxy, F, Cl, Br, —CHF$_2$, —CH$_2$F, —CF$_3$, phenyl, phenoxy, cyano, nitro, amino, dimethylamino and diethylamino; a residue selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, imidazolidinyl, tetrahydrofuranyl (tetrahydrofuryl), piperidinyl, piperazinyl and morpholinyl, which optionally may be substituted with 1, 2, 3, 4 or 5 substituents selected from the group consisting of methyl, ethyl, n-propyl, iso-propyl, n-butyl, sec-butyl, tert.-butyl, methoxy, ethoxy, n-propoxy, n-butoxy, tert.-butoxy, hydroxy, F, Cl, Br, —CHF$_2$, —CH$_2$F, —CF$_3$, phenyl, phenoxy, cyano, nitro, amino, dimethylamino and diethylamino; or a residue selected from the group consisting of phenyl, naphthyl, pyrrolyl, indolyl, furyl, benzo[b]furanyl, thienyl, benzo[b]thienyl, pyrazolyl, imidazolyl, thiazolyl, thiadiazolyl, triazolyl, oxazolyl, isoxazolyl and pyridinyl, which may optionally be substituted with 1, 2, 3, 4 or 5 substituents selected from the group consisting of methyl, ethyl, n-propyl, iso-propyl, n-butyl, sec-butyl, tert.-butyl, methoxy, ethoxy, n-propoxy, n-butoxy, tert.-butoxy, hydroxy, F, Cl, Br, —CHF$_2$, —CH$_2$F, —CF$_3$, phenyl, phenoxy, cyano, nitro, amino, dimethylamino and diethylamino;

R$^{8a}$ denotes a residue selected from the group consisting of methyl, ethyl, n-propyl, iso-propyl, n-butyl, iso-butyl, sec-butyl, tert.-butyl, n-pentyl, iso-pentyl, neopentyl and n-hexyl, which may optionally be substituted with 1, 2, 3, 4 or 5 substituents selected from the group consisting of methoxy, ethoxy, n-propoxy, n-butoxy, tert.-butoxy, hydroxy, F, Cl, Br, —CHF$_2$, —CH$_2$F, —CF$_3$, phenyl, phenoxy, cyano, nitro, amino, dimethylamino and diethylamino; a residue selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, imidazolidinyl, tetrahydrofuranyl, piperidinyl, piperazinyl and morpholinyl, which may optionally be substituted with 1, 2, 3, 4 or 5 substituents selected from the group consisting of methyl, ethyl, n-propyl, iso-propyl, n-butyl, sec-butyl, tert.-butyl, methoxy, ethoxy, n-propoxy, n-butoxy, tert.-butoxy, hydroxy, F, Cl, Br, —CHF$_2$, —CH$_2$F, —CF$_3$, phenyl, phenoxy, cyano, nitro, amino, dimethylamino and diethylamino; or a residue selected from the group consisting of phenyl, naphthyl, pyrrolyl, indolyl, furyl, benzo[b]furanyl, thienyl, benzo[b]thienyl, pyrazolyl, imidazolyl, thiazolyl, thiadiazolyl, triazolyl, oxazolyl, isoxazolyl and pyridinyl, which may optionally be substituted with 1, 2, 3, 4 or 5 substituents selected from the group consisting of methyl, ethyl, n-propyl, iso-propyl, n-butyl, sec-butyl, tert.-butyl, methoxy, ethoxy, n-propoxy, n-butoxy, tert.-butoxy, hydroxy, F, Cl, Br, —CHF$_2$, —CH$_2$F, —CF$_3$, phenyl, phenoxy, cyano, nitro, amino, dimethylamino and diethylamino; and R$^{9a}$ denotes a residue selected from the group consisting of methyl, ethyl, n-propyl, iso-propyl, n-butyl, iso-butyl, sec-butyl, tert.-butyl, n-pentyl, iso-pentyl, neopentyl and n-hexyl, which may optionally be substituted with 1, 2, 3, 4 or 5 substituents selected from the group consisting of methoxy, ethoxy, n-propoxy, n-butoxy, tert.-butoxy, hydroxy, F, Cl, Br, —CHF$_2$, —CH$_2$F, —CF$_3$, phenyl, phenoxy, cyano, nitro, amino, dimethylamino and diethylamino; a residue selected from the group consisting of cyclopropyl, cyclobutyl, cyclopentyl, cyclohexyl, cycloheptyl, cyclooctyl, cyclopentenyl, cyclohexenyl, cycloheptenyl, cyclooctenyl, imidazolidinyl, tetrahydrofuranyl (tetrahydrofuryl), piperidinyl, piperazinyl and morpholinyl, which may optionally be substituted with 1, 2, 3, 4 or 5 substituents selected from the group consisting of methyl, ethyl, n-propyl, iso-propyl, n-butyl, sec-butyl, tert.-butyl, methoxy, ethoxy, n-propoxy, n-butoxy, tert.-butoxy, hydroxy, F, Cl, Br, —CHF$_2$, —CH$_2$F, —CF$_3$, phenyl, phenoxy, cyano, nitro, amino, dimethylamino and diethylamino; or a residue selected from the group consisting of phenyl, naphthyl, pyrrolyl, indolyl, furyl, benzo[b]furanyl, thienyl, benzo[b]thienyl, pyrazolyl, imidazolyl, thiazolyl, thiadiazolyl, triazolyl, oxazolyl, isoxazolyl and pyridinyl, which optionally may be substituted with 1, 2, 3, 4 or 5 substituents selected from the group consisting of methyl, ethyl, n-propyl, iso-propyl, n-butyl, sec-butyl, tert.-butyl, methoxy, ethoxy, n-propoxy, n-butoxy, tert.-butoxy, hydroxy, F, Cl, Br, —CHF$_2$, —CH$_2$F, —CF$_3$, phenyl, phenoxy, cyano, nitro, amino, dimethylamino and diethylamino.

44. A method according to claim 28, wherein:
$R^{1a}$, $R^{2a}$, $R^{3a}$ and $R^{4a}$ independently, respectively denote hydrogen, F, Cl, Br, or a residue selected from the group consisting of methyl, ethyl, n-propyl, iso-propyl, n-butyl, iso-butyl, sec-butyl, tert.-butyl, n-pentyl, iso-pentyl and neopentyl;
$R^{5a}$ denotes a residue selected from the group consisting of phenyl, naphthyl, 2-furyl, 3-furyl, 2-thienyl, 3-thienyl, 2-pyridyl, 3-pyridyl and 4-pyridyl; and
$R^{6a}$ denotes n-hexyl, n-heptyl, n-octyl, n-nonyl, n-decanyl, —(CH$_2$)-phenyl, —(CH$_2$)—(CH$_2$)-phenyl, —(CH$_2$)—(CH$_2$)—(CH$_2$)-phenyl, —C(CH$_3$)$_2$—(CH$_2$)$_3$—CH$_3$ group, —C(CH$_3$)$_2$—(CH$_2$)$_4$—CH$_3$ group, —C(CH$_3$)$_2$—(CH$_2$)$_5$—CH$_3$ group, —C(CH$_3$)$_2$—(CH$_2$)$_6$—CH$_3$ group, C(CH$_3$)$_2$—(CH$_2$)$_7$—CH$_3$ group, or a 1,1,3,3-tetramethylbutyl group.

45. A method according to claim 25, wherein said substituted imidazo[1,2-a]pyridine compound is selected from the group consisting of:
(5,7-dimethyl-2-thiophen-3-yl-imidazo[1,2-a]pyridin-3-yl)-(1,1,3,3-tetramethylbutyl)-amine,
(1,1,3,3-tetramethylbutyl)-(2-thiophen-3-yl-imidazo[1,2-a]pyridin-3-yl)amine,
(7-methyl-2-thiophen-3-yl-imidazo[1,2-a]pyridine-3-yl)-(1,1,3,3-tetramethylbutyl)-amine,
(2-furan-3-yl-imidazo[1,2-a]pyridin-3-yl)-(1,1,3,3-tetramethylbutyl)amine,
(2-furan-3-yl-7-methyl-imidazo[1,2-a]pyridin-3-yl)-(1,1,3,3-tetramethylbutyl)amine,
(2-furan-3-yl-imidazo[1,2-a]pyridine-3-yl)-heptyl-amine,
(1,1-dimethyl-hexyl)-(2-furan-3-yl-imidazo[1,2-a]pyridin-3-yl)-amine,
(1,1-dimethyl-octyl)-(2-furan-3-yl-imidazo[1,2-a]pyridin-3-yl)-amine,
heptyl-(2-thiophen-3-yl-imidazo[1,2-a]pyridin-3-yl)-amine,
(1,1-dimethyl-hexyl)-(2-thiophene-3-yl-imidazo[1,2-a]pyridine-3-yl)-amine,
(2-furan-3-yl-7-methyl-imidazo[1,2-a]pyridin-3-yl)-heptyl-amine,
(2-furan-3-yl-7-methyl-imidazo[1,2-a]pyridin-3-yl)-octyl-amine,
(2-furan-3-yl-7-methyl-imidazo[1,2-a]pyridin-3-yl)-nonyl-amine,
(1,1-dimethyl-hexyl)-(2-furan-3-yl-7-methyl-imidazo[1,2-a]pyridin-3-yl)-amine,
(1,1-dimethyl-heptyl)-(2-furan-3-yl-7-methyl-imidazo[1,2-a]pyridin-3-yl)-amine,
(1,1-dimethyl-octyl)-(2-furan-3-yl-7-methyl-imidazo[1,2-a]pyridin-3-yl)-amine,
(1,1-dimethyl-hexyl)-(7-methyl-2-thiophen-3-yl-imidazo[1,2-a]pyridin-3-yl)-amine,
(1,1-dimethyl-heptyl)-(7-methyl-2-thiophen-3-yl-imidazo[1,2-a]pyridin-3-yl)-amine,
(1,1-dimethyl-octyl)-(7-methyl-2-thiophen-3-yl-imidazo[1,2-a]pyridin-3-yl)-amine,
(7-methyl-2-pyridin-2-yl-imidazo[1,2-a]pyridin-3-yl)-octyl-amine,
(1,1-dimethyl-hexyl)-(7-methyl-2-pyridin-2-yl-imidazo[1,2-a]pyridin-3-yl)-amine,
(1,1-dimethyl-octyl)-(7-methyl-2-pyridin-2-yl-imidazo[1,2-a] pyridin-3-yl)-amine,
(7-methyl-2-pyridine-3-yl-imidazo[1,2-a]pyridin-3-yl)-nonyl-amine,
heptyl-(7-methyl-2-pyridin-4-yl-imidazo[1,2-a]pyridin-3-yl)-amine,
(7-methyl-2-pyridin-4-yl-imidazo[1,2-a]pyridin-3-yl)-octyl-amine,
(1,1-dimethyl-hexyl)-(7-methyl-2-pyridin-4-yl-imidazo[1,2-a]pyridin-3-yl)-amine,
(2-furan-3-yl-6-methyl-imidazo[1,2-a]pyridin-3-yl)-octyl-amine,
(1,1-dimethyl-hexyl)-(2-furan-3-yl-6-methyl-imidazo[1,2-a]pyridin-3-yl)-amine,
(1,1-dimethyl-heptyl)-(6-methyl-2-pyridin-2-yl-imidazo[1,2-a]pyridin-3-yl)-amine,
(1,1-dimethyl-heptyl)-(5-methyl-2-pyridin-2-yl-imidazo[1,2-a]pyridin-3-yl)-amine,
benzyl-(7-methyl-2-thiophen-3-yl-imidazo[1,2-a]pyridin-3-yl)-amine,
(1,1-dimethyl-hexyl)-(7-methyl-2-phenyl-imidazo[1,2-a]pyridin-3-yl)-amine, and
(1,1-dimethyl-hexyl)-(2-furan-3-yl-7-methyl-imidazo[1,2-a]pyridin-3-yl)-amine,
in the form of a pure stereoisomer or a mixture of stereoisomers in any mixing ratio, or a corresponding salt thereof.

* * * * *